(12) United States Patent
Felber et al.

(10) Patent No.: US 11,980,747 B2
(45) Date of Patent: *May 14, 2024

(54) ACOUSTIC DETECTION OF A USAGE OF AN INJECTION DEVICE

(71) Applicant: Sanofi, Paris (FR)

(72) Inventors: Matthias Felber, Winterthur (CH); Nathanael Wettstein, Seuzach (CH); August Enzler, Wil (CH); Felix Kramer, Wil (CH)

(73) Assignee: Sanofi, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,294

(22) Filed: Feb. 21, 2023

(65) Prior Publication Data

US 2023/0191039 A1    Jun. 22, 2023

Related U.S. Application Data

(63) Continuation of application No. 16/954,652, filed as application No. PCT/EP2018/085393 on Dec. 18, 2018, now Pat. No. 11,607,501.

(30) Foreign Application Priority Data

Dec. 21, 2017    (EP) ..................... 17306867

(51) Int. Cl.
*A61M 5/315*    (2006.01)
*A61M 5/31*    (2006.01)
(Continued)

(52) U.S. Cl.
CPC ........ *A61M 5/3157* (2013.01); *A61M 5/5086* (2013.01); *G01F 23/2968* (2013.01);
(Continued)

(58) Field of Classification Search
CPC .............. A61M 5/3157; A61M 5/5086; A61M 2005/3126; A61M 2205/3375;
(Continued)

(56) References Cited

U.S. PATENT DOCUMENTS

2007/0219597 A1* 9/2007 Kamen ............. A61M 5/16809
604/404
2008/0314978 A1 12/2008 Fedorko et al.
(Continued)

FOREIGN PATENT DOCUMENTS

CN    1592643    3/2005
CN    102076332    5/2011
(Continued)

OTHER PUBLICATIONS

International Preliminary Report on Patentability in International Appln. No. PCT/EP2018/085393, dated Jun. 23, 2020, 9 pages.
(Continued)

*Primary Examiner* — Ariana Zimbouski
*Assistant Examiner* — Rachel T. Smith
(74) *Attorney, Agent, or Firm* — Fish & Richardson P.C.

(57) ABSTRACT

Implementations of the present disclosure are directed to an injection device (102) including a medicament reservoir (103) configured to store a medicament to be expelled by the injection device (102), an acoustic source (122*a*, 122*b*, 122*c*, 122*d*, 200, 300, 400) configured to generate an acoustic signal including information indicative of an amount of the medicament stored in the medicament reservoir (103), the acoustic signal being transmitted to an external device (104) configured to process the acoustic signal and to extract injection device data.

19 Claims, 17 Drawing Sheets

(51) Int. Cl.
*A61M 5/50* (2006.01)
*G01F 23/296* (2022.01)

(52) U.S. Cl.
CPC ............... *A61M 2005/3126* (2013.01); *A61M 2205/3375* (2013.01); *A61M 2205/3389* (2013.01); *A61M 2205/3576* (2013.01); *A61M 2205/43* (2013.01)

(58) Field of Classification Search
CPC .. A61M 2205/3389; A61M 2205/3576; A61M 2205/43; A61M 2205/3569; A61M 2205/52; A61M 2205/80; A61M 2205/8243; A61M 5/31568; A61M 2205/60; A61M 2205/35; A61M 5/172; A61M 5/178; A61M 5/31; A61M 5/31566; G01F 23/2968
See application file for complete search history.

(56) References Cited

U.S. PATENT DOCUMENTS

| | | | |
|---|---|---|---|
| 2015/0290396 A1 | 10/2015 | Nagar et al. | |
| 2016/0030683 A1 | 2/2016 | Taylor et al. | |
| 2017/0354366 A1 | 12/2017 | Steensberg | |
| 2018/0200452 A1* | 7/2018 | Marcoz | G01R 33/0206 |
| 2018/0280624 A1* | 10/2018 | Bitton | A61M 5/3155 |
| 2020/0306452 A1 | 10/2020 | Felber et al. | |

FOREIGN PATENT DOCUMENTS

| | | |
|---|---|---|
| CN | 203104783 | 7/2013 |
| CN | 104220116 | 12/2014 |
| CN | 106796744 | 5/2017 |
| DE | 19540456 | 5/1997 |
| EP | 3162398 | 5/2017 |
| JP | 2014-528784 A | 10/2014 |
| JP | 2016-140072 | 8/2016 |
| JP | 2017-534392 | 11/2017 |
| WO | WO 2003/026558 | 4/2003 |
| WO | WO 2009/140251 | 11/2009 |
| WO | WO 2013/040055 | 3/2013 |
| WO | WO 2013/120777 | 8/2013 |
| WO | WO 2015/179015 | 11/2015 |
| WO | WO 2016/071912 | 5/2016 |
| WO | WO 2016/089871 | 6/2016 |
| WO | WO 2016/118736 | 7/2016 |
| WO | WO 2017/132577 | 8/2017 |

OTHER PUBLICATIONS

International Search Report and Written Opinion in International Appln. No. PCT/EP2018/085393, dated Mar. 19, 2019, 11 pages.

\* cited by examiner

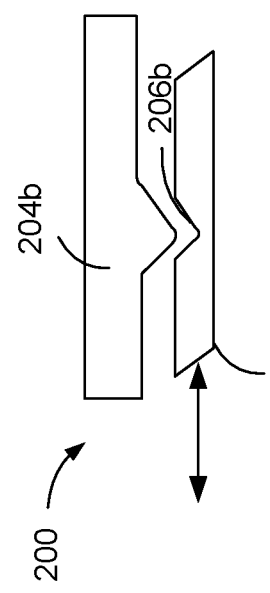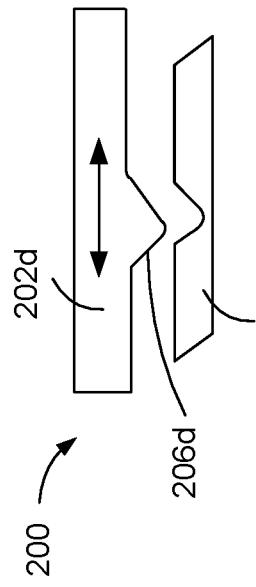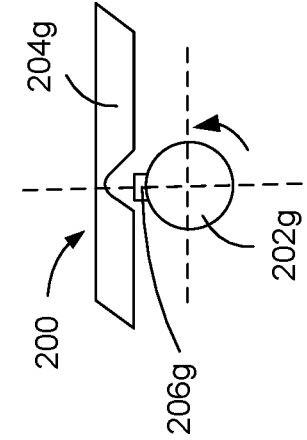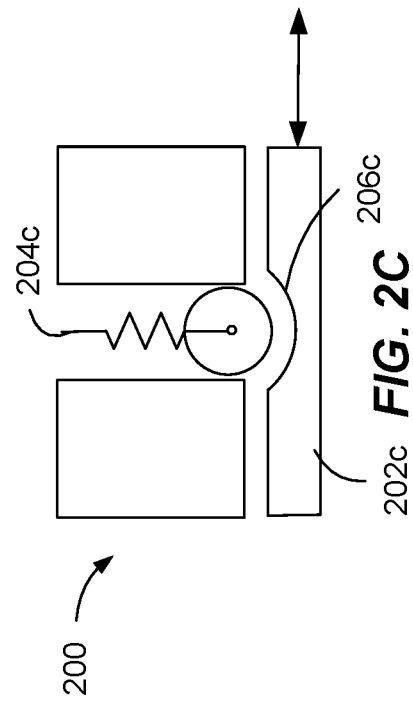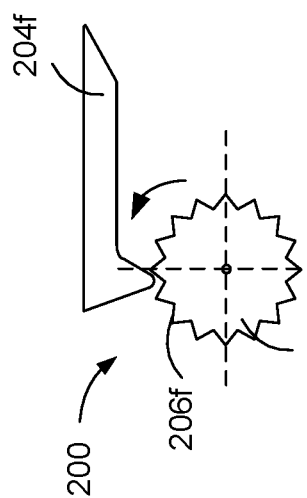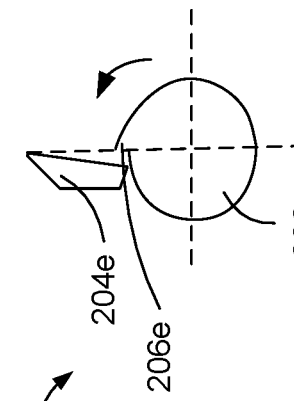

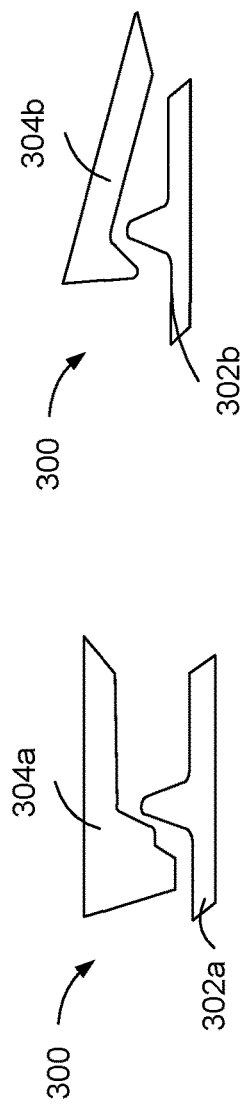
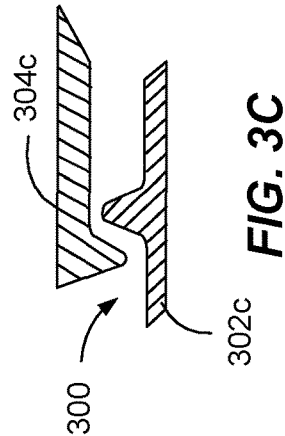
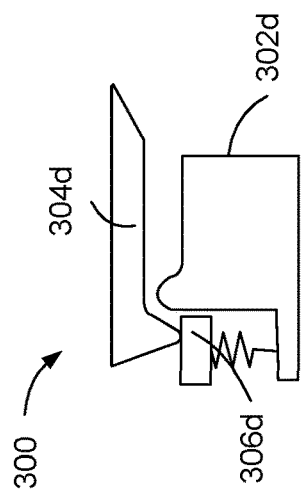
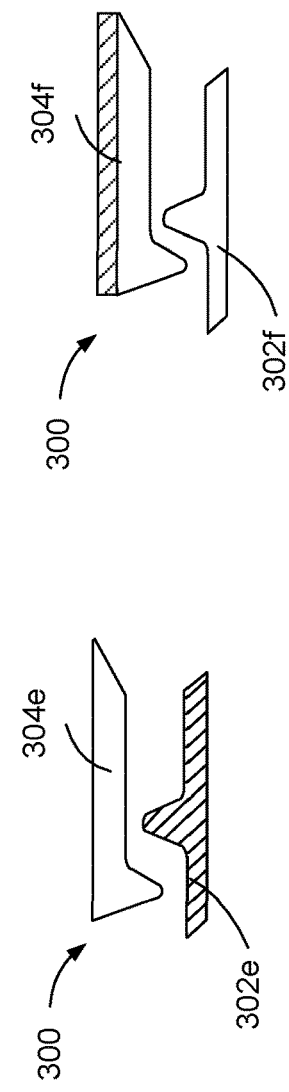
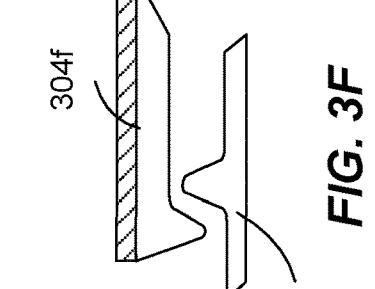
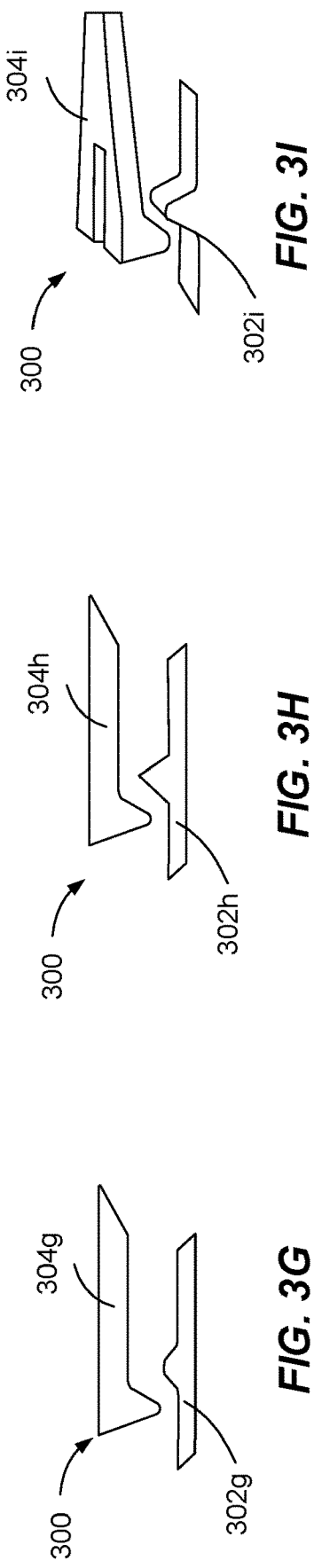

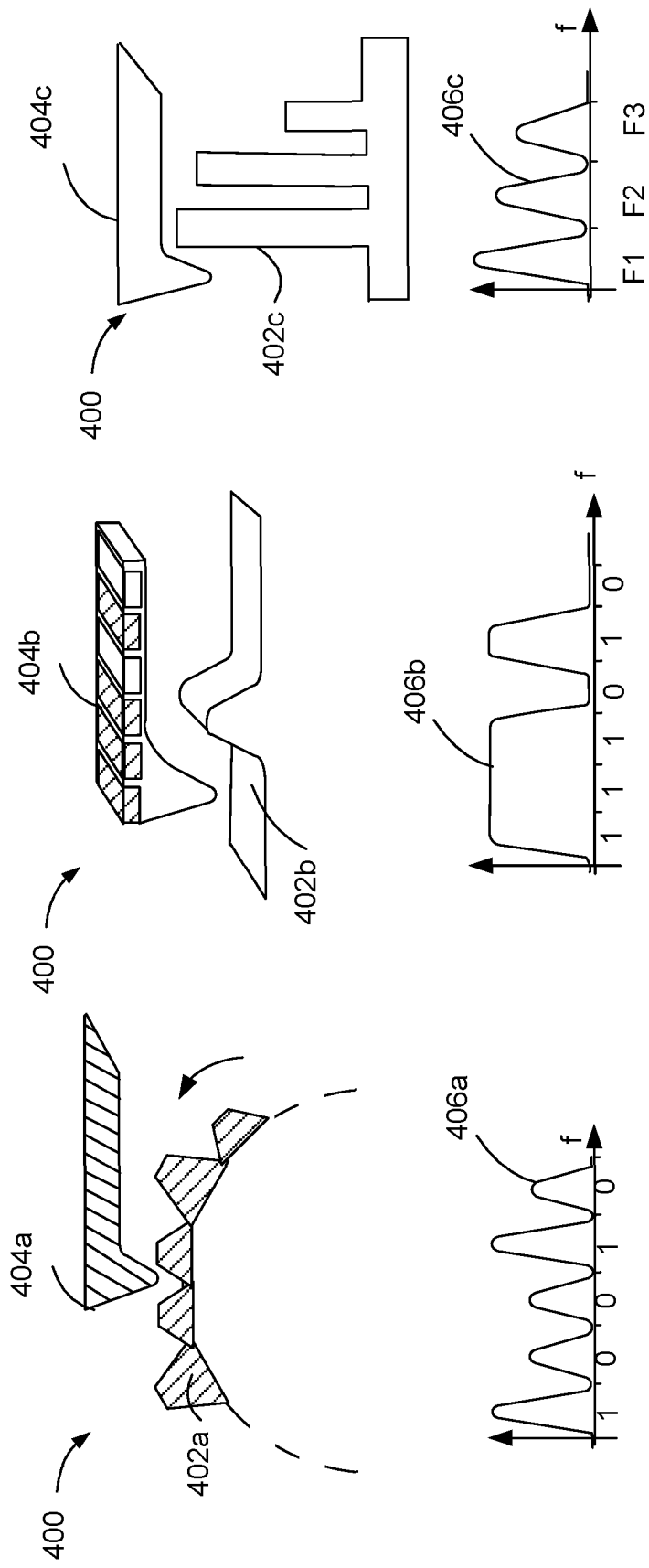

U.S. 11,980,747 B2

ACOUSTIC DETECTION OF A USAGE OF AN INJECTION DEVICE

CROSS-REFERENCE TO RELATED APPLICATIONS

This application is a continuation of U.S. patent application Ser. No. 16/954,652, filed Jun. 17, 2020, which is a § 371 National Stage Application of PCT/EP2018/085393, filed Dec. 18, 2018, which claims the benefit of Application No. EP17306867.7, filed on Dec. 21, 2017, which is incorporated herein by reference in its entirety.

TECHNICAL FIELD

This disclosure relates to detection of a usage of an injection device, and more particularly, to acoustic detection of a usage of an injection device.

BACKGROUND

Electronic injection devices allow patients to safely administer a medicament, without the need for constant supervision by medical staff, while enabling transmission of treatment data to the medical staff. Treatment data is generally transmitted by electronic components that are characterized by a "medium" or "typical" power consumption. Usually, electronic injection devices are powered by a battery integrated within the device or through wired connection by an external energy supply. Both integrated batteries and wired connections present several disadvantages. For example, current configurations of electronic injection devices lead to idle drainage of the energy supply, such that, even if the electronic injection device has not been used, long shelf life can exhaust the life of the battery. A low battery condition can lead to no- or malfunction of the device, an incorrect dosage, a missed dosage, or it can even make the electronic injection device unusable by stopping the operation of the electronic components.

SUMMARY

Implementations of the present disclosure include acoustic detection mechanisms and systems configured for transmitting injection device data with minimum energy consumption. In accordance with one aspect of the present disclosure, a medicament injection system includes an injection device and an external device. The injection device includes a medicament reservoir configured to store a medicament to be expelled by the injection device, and an acoustic source configured to generate an acoustic signal including information indicative of an amount of the medicament stored in the medicament reservoir. The external device includes an acoustic receiver configured to record the acoustic signal and one or more processors configured to process the recorded acoustic signal and to generate injection device data based on the processed recorded acoustic signal. The external device is configured to display information based on the injection device data.

In some implementations, the acoustic source includes a moving element and an inhibition element that produce the acoustic signal by interacting with each other. In some implementations, the moving element includes at least one of a lever-type snapper, a dual-sided lever, a spring-powered element, a rotating cam and a rotating wheel including multiple indents. In some implementations, at least one of the moving element and the inhibition element includes an arrangement of a plurality of materials to generate a sequence of a plurality of frequencies. In some implementations, at least one of the moving element and the inhibition element includes a plurality of geometrical features to generate a sequence of a plurality of frequencies. In some implementations, the sequence of a plurality of frequencies is associated with an identifier of the injection device. In some implementations, the acoustic source includes a vibrating element configured to generate a reverberation within the acoustic signal. In some implementations, the reverberation is associated with an identifier of the injection device. In some implementations, the acoustic source is enclosed within the injection device. In some implementations, a portion of a wall of the injection device that is proximal to the acoustic source defines an opening configured to enhance transmission of the acoustic signal. In some implementations, the opening is covered by a sealing membrane. In some implementations, the acoustic source is attached to an exterior surface of the injection device. In some implementations, the acoustic source is integrated into a dial grip to generate an omnidirectional transmission of the acoustic signal.

In accordance with another aspect of the present disclosure, an injection device includes a medicament reservoir configured to store a medicament to be expelled by the injection device, an acoustic source configured to generate an acoustic signal including information indicative of an amount of the medicament stored in the medicament reservoir, the acoustic signal being transmitted to an external device configured to process the acoustic signal and to extract injection device data.

In accordance with another aspect of the present disclosure, a medicament injection system includes an injection device and an external device. The injection device includes a medicament reservoir configured to store a medicament to be expelled by the injection device, an acoustic source configured to generate an acoustic signal including information indicative of an amount of the medicament stored in the medicament reservoir, an acoustic receiver configured to record the acoustic signal, a control logic configured to process the recorded acoustic signal and to generate an injection device signal based on the processed recorded acoustic signal, and an antenna configured to transmit the injection device signal. The external device includes a receiver configured to receive the injection device signal, and one or more processors configured to process the injection device signal and to generate injection device data based on the processed injection device signal. The external device is configured to display information based on the injection device data.

It is appreciated that systems in accordance with the present disclosure can include any combination of the aspects and features described herein. That is to say that methods in accordance with the present disclosure are not limited to the combinations of aspects and features specifically described herein, but also include any combination of the aspects and features provided.

BRIEF DESCRIPTION OF THE FIGURES

The details of one or more embodiments of the present disclosure are set forth in the accompanying drawings and the description below. Other features and advantages of the present disclosure will be apparent from the description and drawings, and from the claims.

FIGS. 2A-2G are examples of acoustic mechanisms in accordance with the present disclosure.

FIGS. 3A-3I are examples of acoustic mechanisms in accordance with the present disclosure.

FIGS. 4A-4C are examples of acoustic mechanisms in accordance with the present disclosure.

Like reference symbols in the various drawings indicate like elements.

DETAILED DESCRIPTION

Figure 1A:
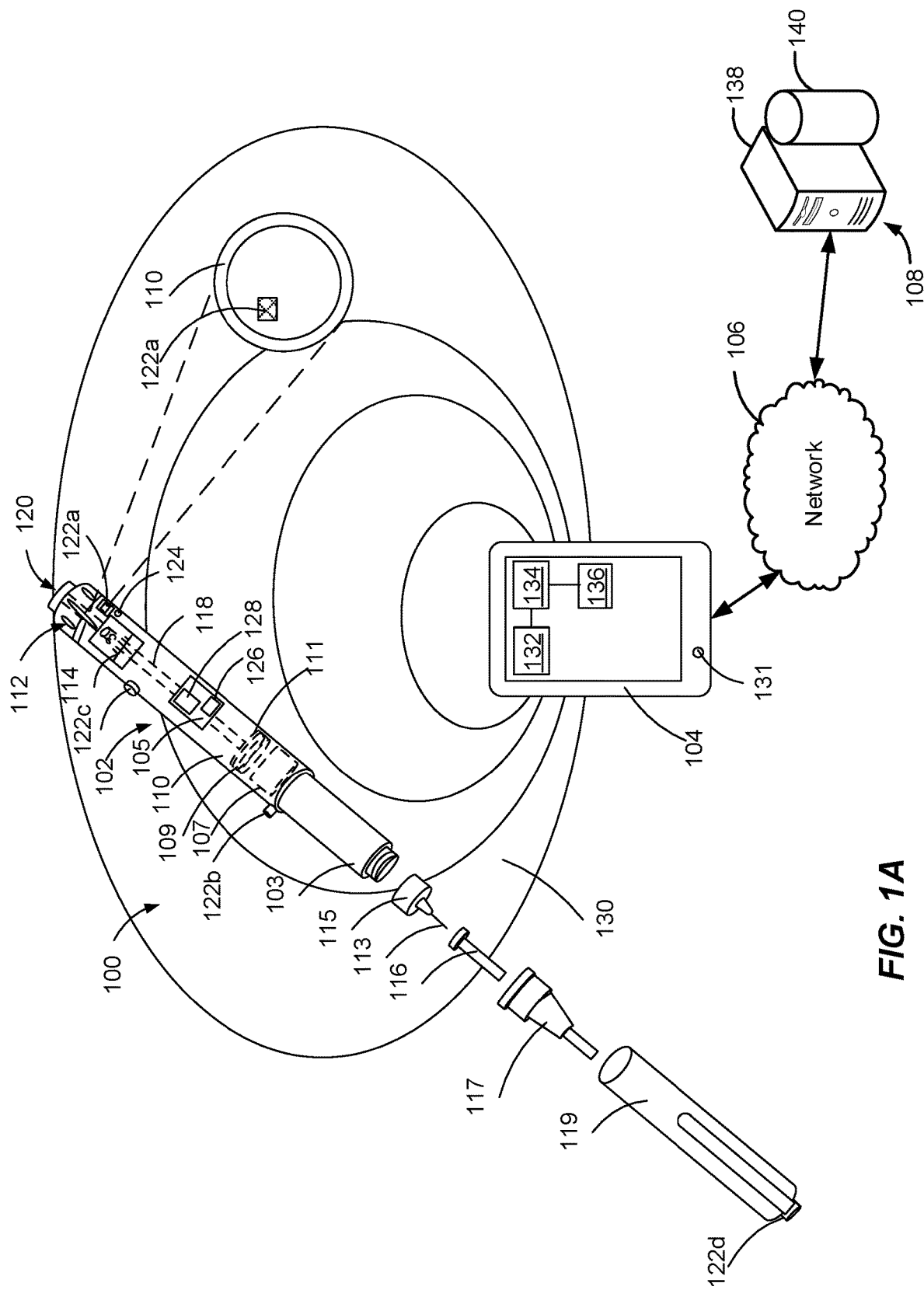
FIGS. 1A-1H are exploded views of examples of devices in accordance with the present disclosure.

Implementations of the present disclosure are generally directed to generating an acoustic signal associated with an operation of an injection device and transmitting injection device data using minimal energy. More particularly, implementations of the present disclosure are directed to directly transmitting acoustic signals including injection device data to an external device and, optionally, harvesting energy to power electronic components of the injection device to collect and transmit additional injection device data.

Electronic components of an electronic injection device may drain the device's energy source even when the device is idle. Accordingly, collection, processing and transmission of injection device data can be hindered by idle drained batteries. As described in further detail herein, implementations of the present disclosure address this challenge. For example, the injection device can include mechanical components that generate acoustic signals associated with an operation of the injection device without a battery or any other type of electric energy supply. Further, the injection device can include mechanical components and electronic components that operate by using energy harvested from the environment. The electronic components of the injection device can be configured for low-power data processing and data transmission. An injection device configured to operate without a battery typically has a low environmental footprint and can be manufactured as a disposable item.

FIGS. 1A-1F depict example systems 100 that can be used to execute implementations of the present disclosure. For example, the example systems 100 can be used for generating acoustic signals and, optionally, for harvesting energy to power electronic components of an injection device 102 to collect and transmit RF signals including injection device data. In the depicted example, the example system 100 includes one or more injection devices 102, an external device 104, a network 106 and a server system 108.

The injection device 102 can be a pre-filled, disposable injection pen or the injection device 102 can be a reusable injection pen. The injection device 102 can be configured to communicate with the external device 104 (e.g., a smart phone configured to generate RF signals). For example, the injection device 102 can be configured to generate acoustic signals that can be detected by the external device 104. The acoustic signals can include a sound signal with a frequency within a frequency range perceptible by a microphone 131 of the external device 104 (e.g., 20 Hz to 20 kHz).

In some implementations, the injection device 102 can be configured to harvest energy from the external device 104 and to transmit injection device data to the external device 104. Energy harvesting defines the process of wireless electrical charging of the injection device 102 using the external device 104 or an external source as an energy distributor. The process of energy harvesting includes capturing RF signals generated by the external device 104, converting the RF signals to electric signals, and boosting the electric signals to feed one or more components of the injection device with electric energy. The injection device 102 can transmit to the external device 104 operational data (e.g., date and time of start of usage of injection device 102 and sensor measurements) and corresponding treatment data (e.g., amount and time of medicament dispense by the injection device 102). In some implementations, the injection device 102 can be associated with an identifier that is used by the external device 104 to uniquely identify the injection device 102.

The injection device 102 can include a housing 110 and a needle assembly 115. The housing 110 can be molded from a medical grade plastic material such as a liquid crystal polymer cyclic olefin copolymer (COC), cyclo-olefin polymer (COP) or glass. The housing 110 can be configured to be at least partially covered by a cap 119 during storage of the injection device. The housing 110 can contain a medicament reservoir 103, an electronic module 105, a stopper 107, a plunger rod 118, a plunger head 109, a bearing 111, a dial grip 112, a dosage window 114, an injection button 120, one or more acoustic sources 122a, 122b, 122c, 122d and, optionally, an acoustic receiver 124.

The medicament reservoir 103 can be configured to contain a fluid medicament. The medicament can include a pharmaceutical formulation containing at least one pharmaceutically active compound. The medicament can include insulin analogs, insulin derivatives, analgesics, hormones, beta agonists, corticosteroids, or a combination of any of the above-mentioned drugs. The medicament reservoir 103 can be a conventional, generally cylindrical, disposable container like a cartridge or a syringe used to package prepared fluids such as medicaments, anesthetics and the like. The medicament reservoir 103 can be provided with a pair of ends, one end having a pierceable membrane, which receives an inward end of needle 113 in a liquid tight sealing engagement and the other end, close to the dial grip 112, being open, such that the stopper 107 can slide through it and move towards a needle 113 when dispensing the medicament.

A dose of the medicament contained in the medicament reservoir 103 can be ejected from the injection device 102 by turning the dial grip 112, which actuates one of the acoustic sources 122a, 122b, 122c, 122d to generate a mechanical click sound. The selected dose is displayed via dosage window 114, for instance in multiples of so-called International Units (IU), wherein one IU is the biological equivalent of about 45.5 micrograms of pure crystalline medicament (1/22 mg). An example of a selected dose displayed in dosage window 114 may for instance be 30 IUs, as shown in FIG. 1. The numbers displayed in dosage window 114 can be printed on a sleeve that is contained in housing 110 and mechanically interacts with a plunger head 109 that is fixed at the end of the plunger rod 118 and pushes the stopper 107 of the medicament reservoir 103. In some implementations, the selected dose can be displayed differently, for instance by an electronic display (e.g., the dosage window 114 may take the form of an electronic display). The bearing 111 can provide firm mounting to one or both ends of the plunger rod 118.

The plunger head 109 (e.g., a back end of the plunger) can be configured to expel a portion of the fluid by displacing the stopper 107 contained within the medicament reservoir 103, such that a position of the stopper 107 is associated with an amount of the fluid within the injection device 102. The stopper 107 can be a flexible stopper, such as a rubber stopper. The stopper 107 can be of a sufficient length so that the stopper 107 is not ripped or twisted when being engaged by the plunger head 109.

The needle assembly 115 includes a needle 113 that can be affixed to the housing 110. The needle 113 can be covered by an inner needle cap 116 and an outer needle cap 117, which in turn can be covered by a cap 119. When needle 113 is stuck into a skin portion of a patient, and then injection button 120 is pushed, the medicament dose displayed in display window 114 can be ejected from injection device 102. When the needle 113 of injection device 102 remains for a certain time in the skin portion after the injection button 120 is pushed, a high percentage of the dose (e.g., more than approximately 95%) is actually injected into the patient's body. Ejection of the medicament dose can actuate one of the acoustic sources 122a, 122b, 122c, 122d to generate a mechanical click sound, which can be different from sounds produced when using dial grip 112, which actuates a different one of the acoustic sources 122a, 122b, 122c, 122d. Injection device 102 can be used for several injection processes until either medicament reservoir 103 is empty or the expiration date of injection device 102 (e.g., 28 days after the first use) is reached.

Before using injection device 102 for the first time, it may be necessary to perform a priming operation to generate an acoustic signal and, optionally, to harvest energy from the external source and/or to remove air from medicament reservoir 103 and needle 113. For instance, the priming operation can include actuating acoustic sources 122a, 122b, 122c, 122d turning the dial grip 112 to select one or two units of medicament and pressing injection button 120 while holding injection device 102 with the needle 113 upwards. Turning the dial grip 112 can cause a mechanical click sound to provide acoustic feedback to a user.

Each of the acoustic sources 122a, 122b, 122c, 122d includes an acoustic mechanism configured to generate a unique acoustic signal, for example with a unique frequency pattern that can be differentiated from the acoustic signal of other acoustic sources. The acoustic mechanisms of the acoustic sources 122a, 122b, 122c, 122d can include pressure elements (e.g., buttons), rotating elements (e.g., rotating knobs, rotating cams, or rotating wheels), inhibition elements (e.g., protrusions), vibration elements, latching elements, flexible elements, swinging elements, attenuation elements, and other mechanical elements, as described in detail with reference to FIGS. 2-4. The acoustic sources 122a, 122b, 122c, 122d can be attached to or integrated within the injection device 102 at different locations.

For example, an acoustic source 122a can be located within the housing 110 near to a moving element, such as the plunger rod 118, the plunger head 109, the bearing 111, the dial grip 112, the dosage window 114, and/or the injection button 120. As a further example, an acoustic source 122b (e.g., a button) can be located on a section of the housing 110 that is covered by the cap 119 when the cap is on and can be activated during removal of the cap 119 or during recapping of the injection device 102. As a further example, an acoustic source 122c (e.g., a button or rotating knob) can be located on the surface of the housing 110 at a location independent from other components to be activated by a user of the injection device 102. The acoustic source 122c being located on the surface of the housing 110, is substantially not affected by the body of the injection device 102 and is characterized by optimal directionality (e.g., is transmitted equally in all directions). As a further example, an acoustic source 122d (e.g., a button) can be located on the cap 119 to generate an acoustic signal associated with a particular tapping motion performed by a user of the injection device 102.

In some implementations, as illustrated in FIG. 1A, the acoustic source 122a is completely covered by the walls of the housing 110 and the acoustic receiver 124 is near to (e.g., 1-10 mm away from) the acoustic source 122a. The acoustic signal produced by the acoustic source 122a covered by the walls of the housing 110 is attenuated by one or more components of the injection device 102.

Figure 1B:
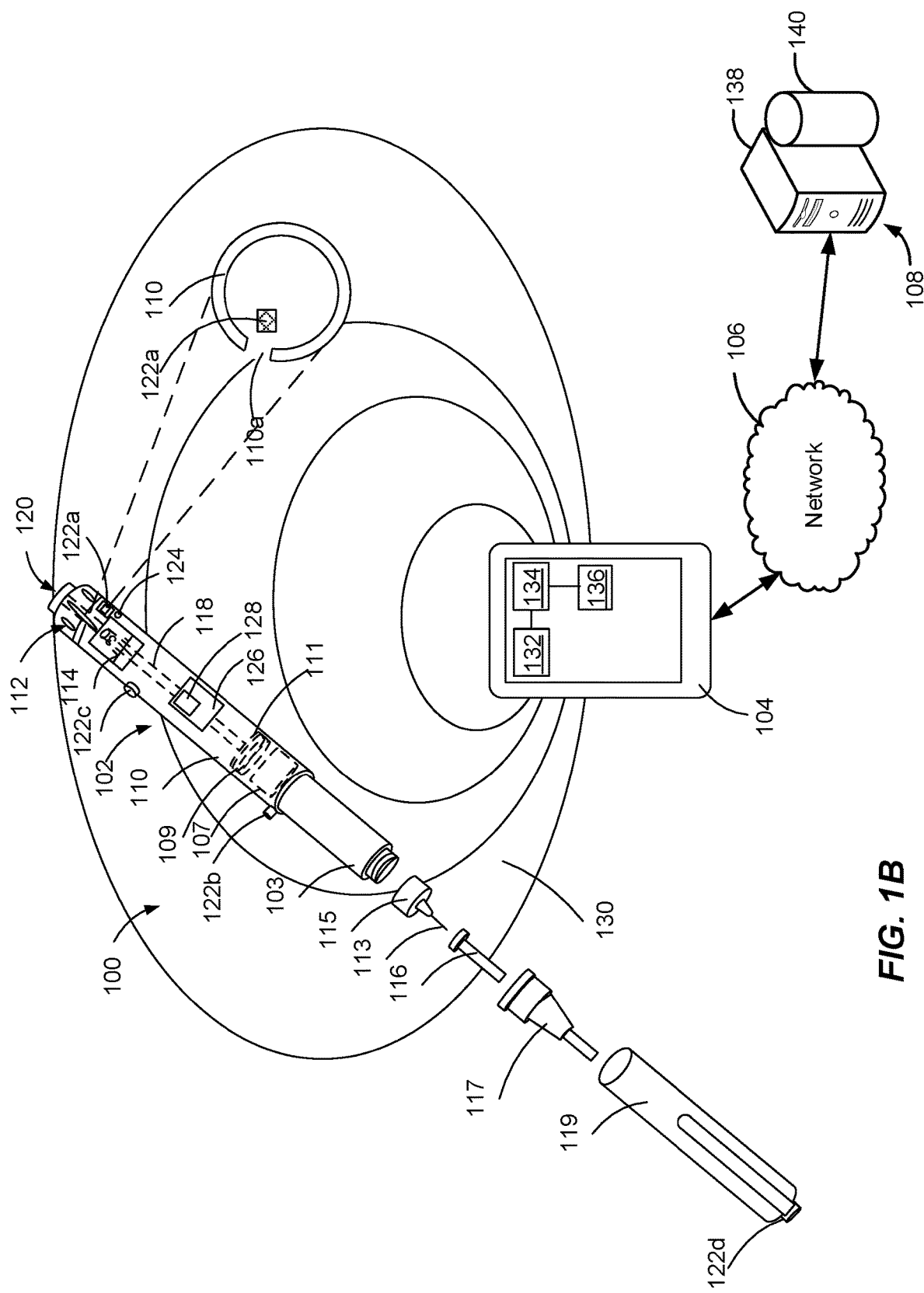
Figure 1C:
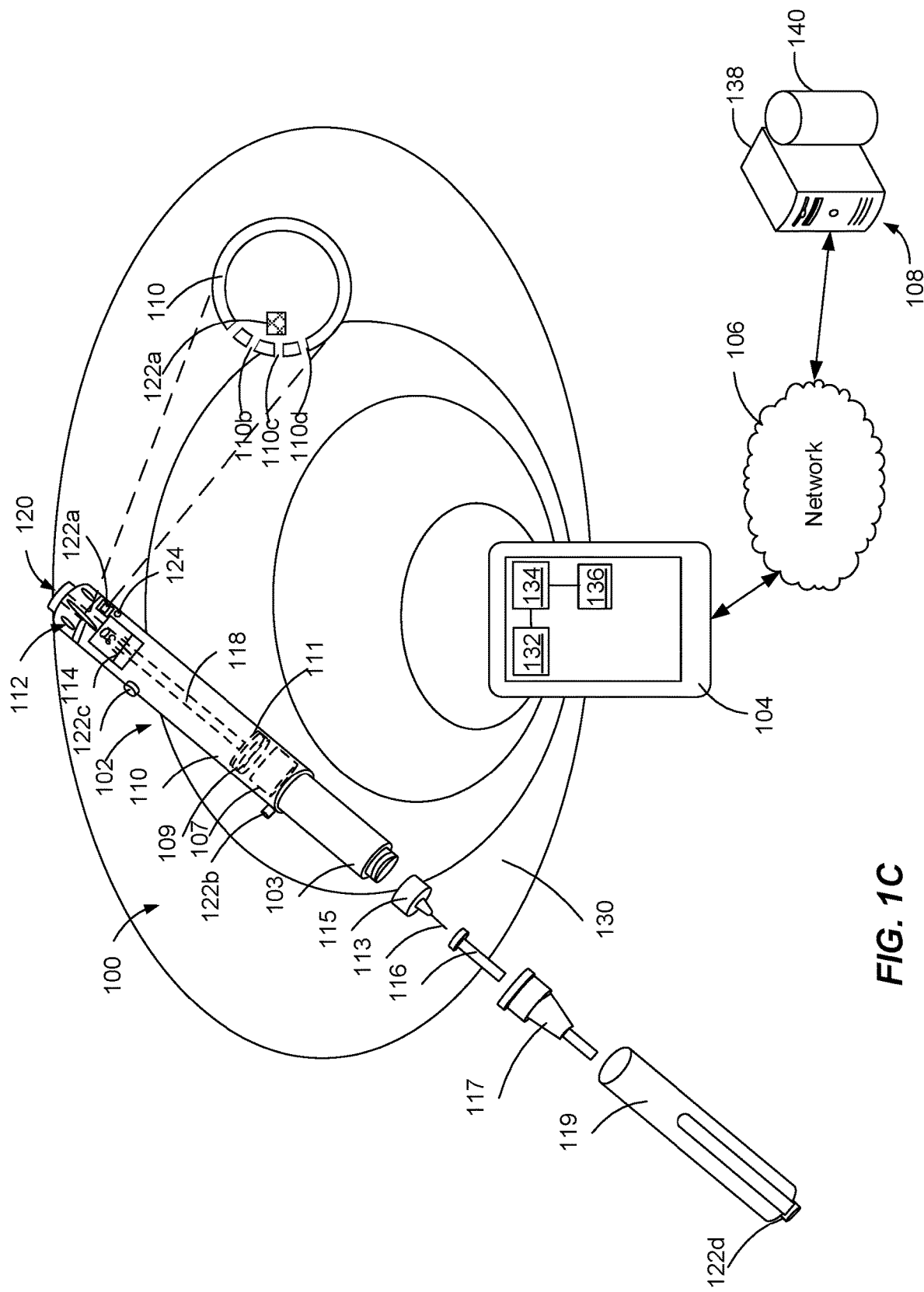

In some implementations, as illustrated in FIG. 1B, the walls of the housing 110 can include an opening 110a adjacent to the acoustic source 122a and the acoustic receiver 124 is near to (e.g., 1-10 mm away from) the acoustic source 122a. The opening 110a can have a diameter within the range from about 0.5 mm to about 9 mm. The acoustic signal produced adjacent to the opening 110a is a directional signal that is transmitted without attenuation through the opening 110a while being attenuated in other directions that include transmission through the walls of the housing 110.

In some implementations, as illustrated in FIG. 10, the walls of the housing 110 can include a plurality of openings 110b, 110c, 110d adjacent to the acoustic source 122a and the acoustic receiver 124 is near to (e.g., 1-10 mm away from) the openings 110b, 110c, 110d. The openings 110b, 110c, 110d can have a small diameter (e.g., smaller than 1 mm) that prevents any mechanical interference with the inner components of the injection device 102. For example, the openings 110b, 110c, 110d can have a diameter within the range from about 0.1 mm to about 2 mm. The acoustic signal produced adjacent to the opening 110a is a directional signal that is transmitted without attenuation through the openings 110b, 110c, 110d while being attenuated in other directions that include transmission through the walls of the housing 110.

Figure 1D:
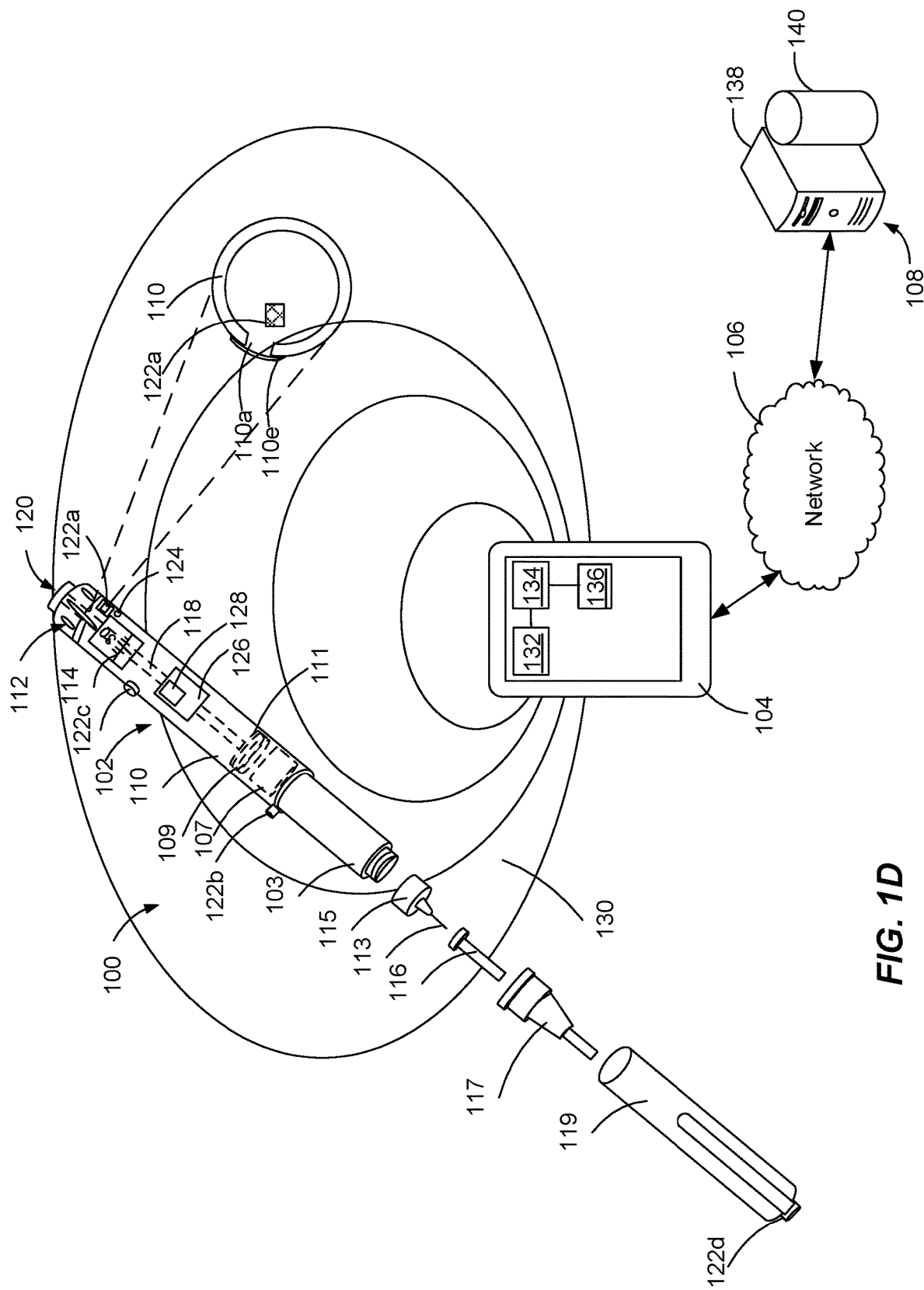
Figure 1E:
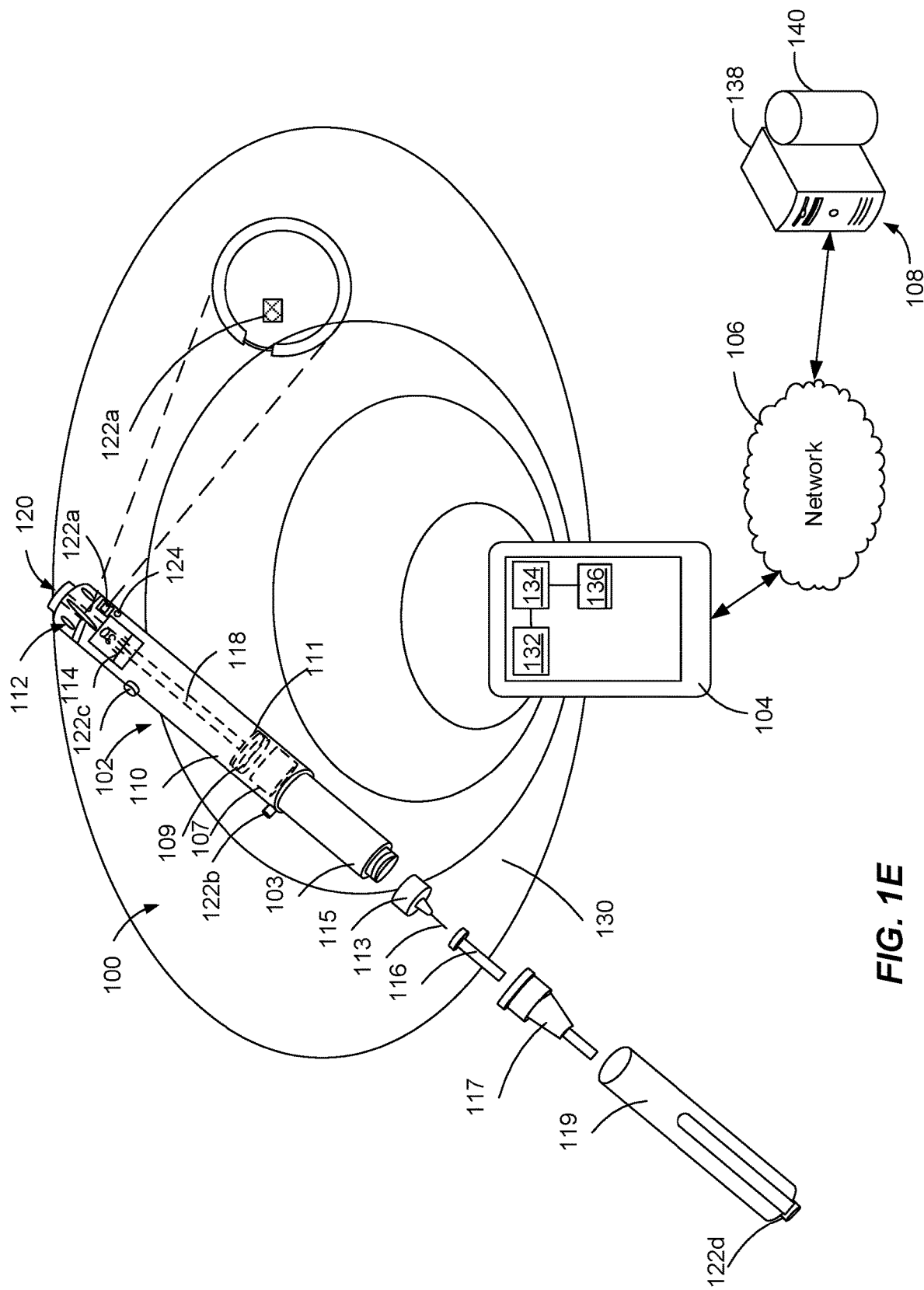

In some implementations, as illustrated in FIGS. 1D and 1E, the walls of the housing 110 can include an opening 110a covered by a thin membrane 110e (e.g., with a thickness smaller than about 1 mm) adjacent to the acoustic source 122a and an acoustic receiver 124 near to (e.g., 1-40 mm away from) the acoustic source 122a. The membrane 110e can be configured to transmit the acoustic signal substantially without attenuation (e.g., by decreasing the amplitude of the acoustic signal less than approximately 5%). The membrane 110e can be configured to seal the opening 110a by preventing contamination of and/or interference with components of the injections device. The membrane 110e can have a diameter equal to or larger than the opening 110a and can be attached to the surface of the housing 110, such as a label (e.g., FIG. 1D). The membrane 110e can have a diameter equal to the opening 110a and can be fixed within the opening 110a (e.g., FIG. 1E).

Figure 1F:
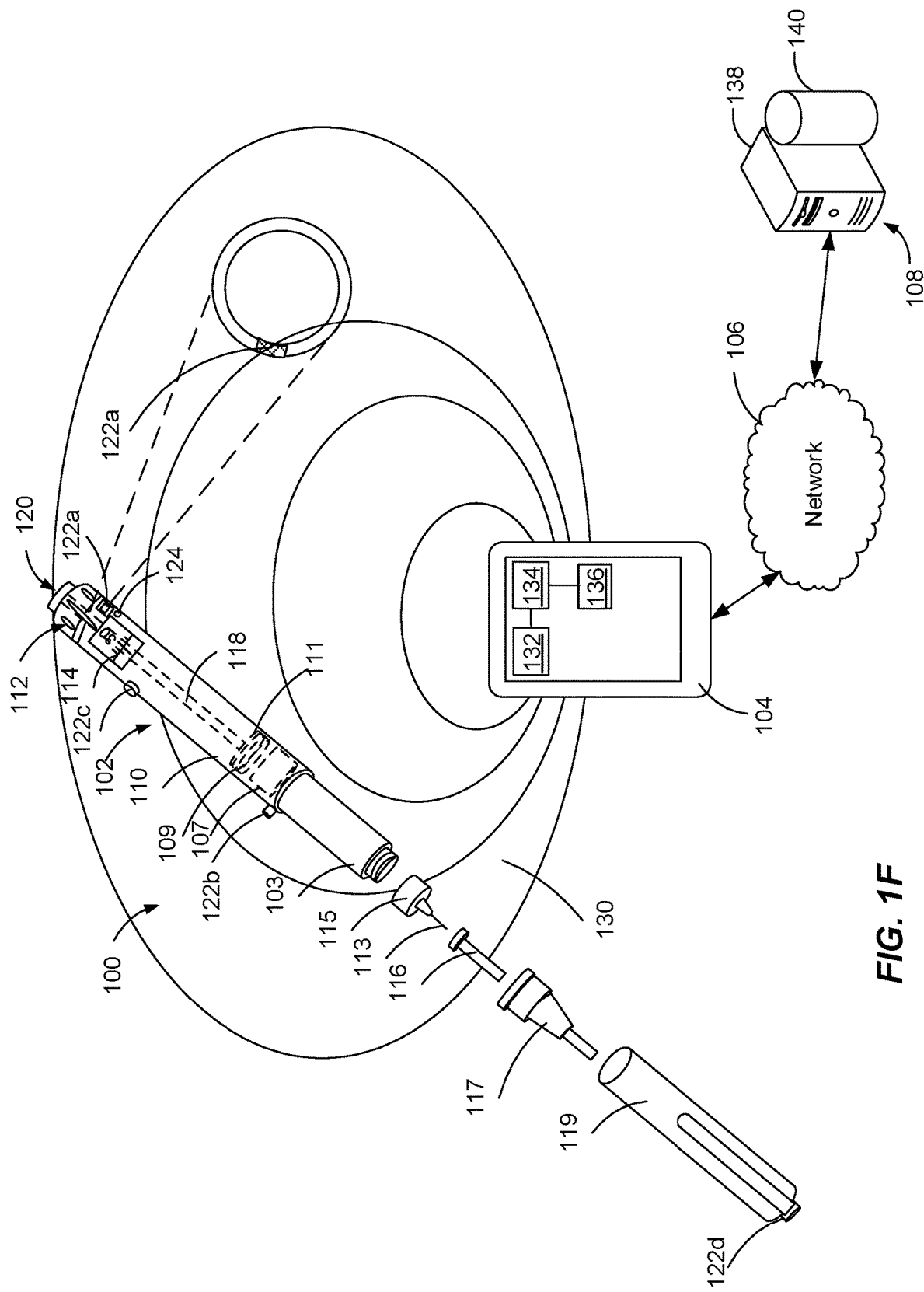
Figure 1G:
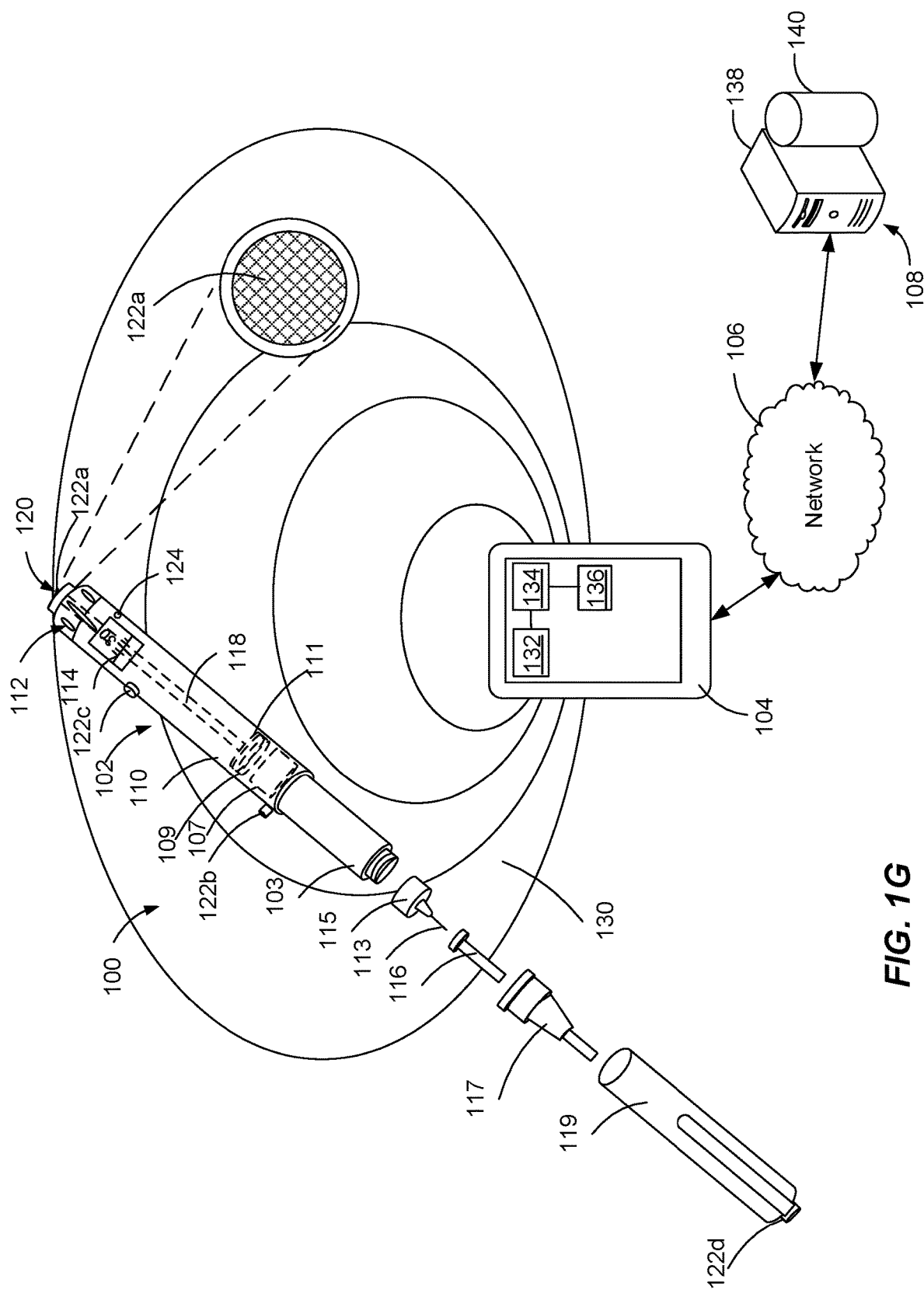

In some implementations, as illustrated in FIG. 1F, the acoustic source 122a is embedded within a portion of a wall of the housing 110 and the acoustic receiver 124 is near to (e.g., approximately 1 mm to approximately 40 mm away from) the acoustic source 122a. The acoustic signal produced by the acoustic source 122a is embedded within the housing 110 is a directional signal that is transmitted without attenuation in a forward direction while being attenuated in other directions that include transmission through the walls of the housing 110. In some implementations, as illustrated in FIG. 1G, the acoustic source 122a is directly attached to a portion of an inner wall of the housing 110. The acoustic signal produced by the acoustic source 122a covered by the walls of the housing 110 is attenuated by one or more components of the injection device 102.

Figure 1H:
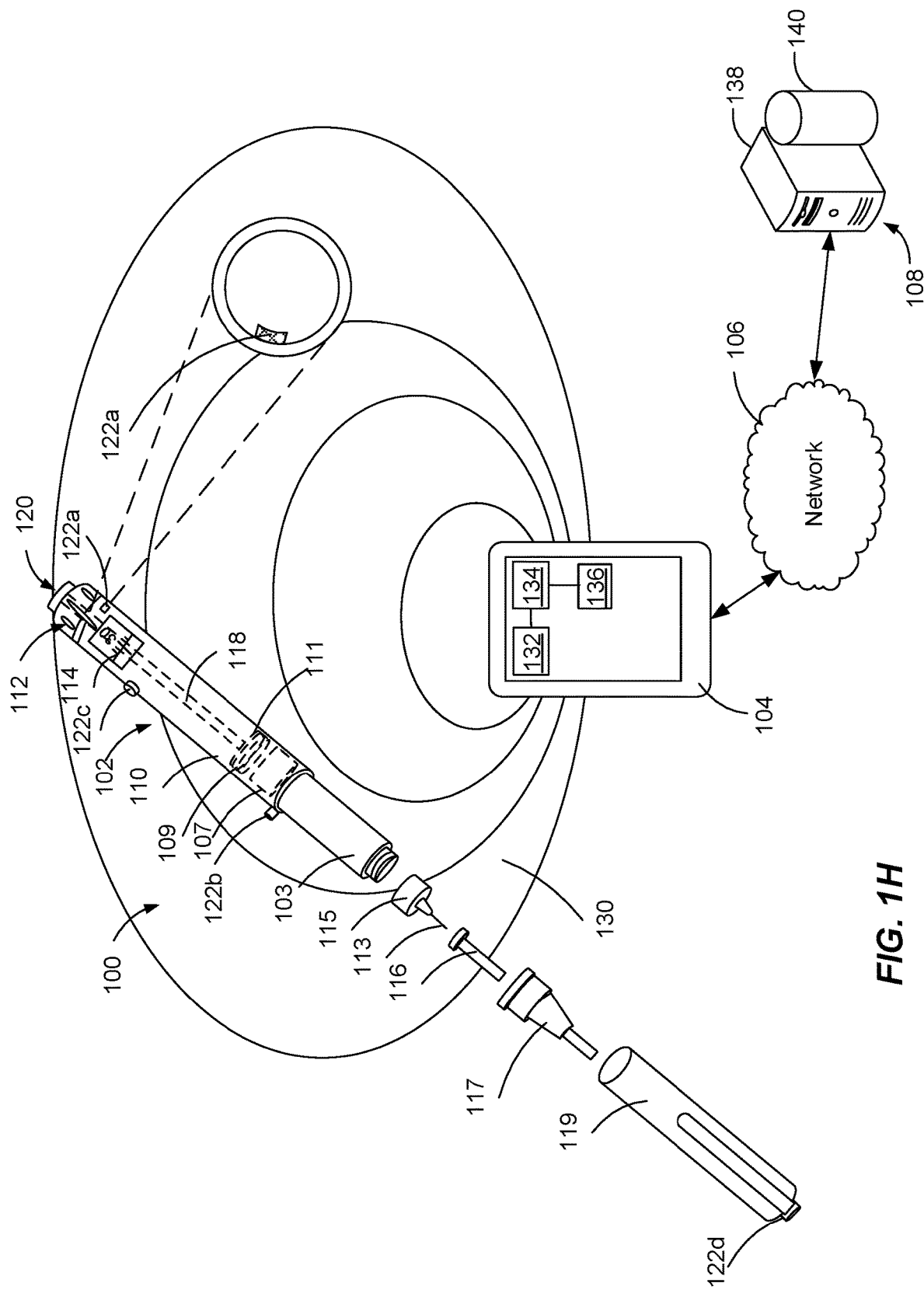

In some implementations, as illustrated in FIG. 1H, the acoustic source 122a is integrated within the dial grip 112 and the acoustic receiver 124 is near (e.g., 1-40 mm away from) to the acoustic source 122a. The damping effects of the acoustic signal produced by the acoustic source 122a embedded within the dial grip 112 can be minimized if the acoustic source 122a is a mechanically decoupled part. The acoustic signal produced by the acoustic source 122a embedded within the dial grip 112 is substantially omnidirectional. FIG. 1G illustrates the injection device 102 without an acoustic receiver 124. However, it can be understood that any configuration of the acoustic source 122a (as described with reference to FIGS. 1A-1H) is possible without the acoustic receiver 124.

In some implementations, the acoustic signal generated by one of the acoustic sources 122a, 122b, 122c, 122d can initiate a communication between the electronic module 105 and the external device 104. The electronic module 105 can be configured to perform and/or assist with one or more functions of the injection device 102 (e.g., the ejection of the medicament). The electronic module 105 can be molded within a component of the injection device 102 or attached to the injection device 102. The electronic module 105 can include an electronic component 126 and an antenna 128.

In some implementations, the electronic component 126 can include a sensor configured to detect a signal including an indication of medicament amount associated with a function of the injection device 102 and to generate a sensor signal based on the signal. The function can include an operation of the injection device associated with dispensing a medicament amount, such as a displacement of the plunger rod 118. The signal including the indication of medicament amount can include an electric signal, an acoustic signal, a mechanical signal, and/or an optical signal. For example, the sensor can be configured to generate an electric signal that is proportionate to an amount of medicament stored in the medicament reservoir 103 or dispensed by the injection device 102. Further, the sensor can include a mechanical component, an acoustic component (e.g., a piezo element), an optical component (e.g., pairs of light emitting diodes and photodiodes), a magnetic component (e.g., permanent magnet or plastic containing ferromagnetic particles), an electric component (e.g., capacitive electrode, variable resistance), contact switches or a combination thereof. Further, the sensor can include an incremental dosing sensor configured to measure an amount of expelled medicament. In some implementations, the sensor can be configured to include in addition to the sensor configured to detect a signal indicating the amount of medicament an environmental sensor. The environmental sensor can include any of a temperature sensor, a humidity sensor, an air quality sensor, or a light intensity sensor. In some implementations, multiple sensors can be included in the injection device 102 of FIG. 1 at different locations to detect medicament amount associated data and/or to increase an accuracy of a result associated with the sensor measurements. The sensor can transmit a signal (e.g., a voltage) to the control component 124.

In some implementations, the electronic component 126 can include a control component, such as an ultra-low power (µW) platform chip, operating in a in a power range from tens of µW to nW. The control component can be configured to process the signal received from the acoustic sources 122a, 122b, 122c, 122d and to transmit injection device data using the antenna 128. The antenna 128 can be a radio frequency (RF) ultra-wide band or millimeter wave antenna that can transmit injection device data to the external device 104, as described with reference to FIGS. 5A-5D. The antenna 128 can be electrically insulated from the surface of the injection device 128 to prevent a user interaction from influencing the signal and signal strength. The communication field 130 can enable communication between the injection device 102 and the external device 104. The communication field 130 can be based on an ultra-low power RF transmission protocol. The signals transmitted by the antenna 128 of the injection device 102 can include the amount of the fluid in the medicament reservoir 103, additional environmental values, and the identifier of the injection device 102. In some implementations, the electronic components of the electronic module 105 can be integrated within the housing 110 at a single location or at multiple locations (e.g., fitted within or attached to the plunger rod 118, a cavity in the plunger head 109, a cavity in the stopper 107 or a wall of the medicament reservoir 103). Further details regarding the components and functionalities of the electronic module 105 are provided with reference to FIGS. 5A-5D.

The external device 104 can communicate with the injection device 102 over the communication field 130 and with one or more of the server devices 108 over the network 106. In some implementations, the external device 104 can include any appropriate type of computing device such as a desktop computer, a laptop computer, a handheld computer, a tablet computer, a personal digital assistant (PDA), a cellular telephone, a network appliance, a camera, a smart phone, a smart watch, an enhanced general packet radio service (EGPRS) mobile phone, a media player, a navigation device, an email device, a game console, or an appropriate combination of any two or more of these devices or other data processing devices.

The external device 104 can include a transceiver 132 (e.g., a microphone and an antenna), a processor 134 and a display 136. The transceiver 132 can be configured to transmit signals to activate and/or powers the injection device 102 and receive signals from the injection device 102. The transceiver 132 can be configured to spontaneously transmit signals to the injection device 102 at a pre-set frequency during pre-set time intervals. The processor 134 can be configured to process the data transmitted by the injection device 102. The external device 104 can be configured to enable a user to interact with the display 136 (e.g., through a graphical user interface) to initiate a communication between the external device 102 and the injection device 102. The display 136 can be configured to display the data received from the injection device 102 and processed by the external processor 134. Further details regarding the components and functionalities of the external device 104 are provided with reference to FIGS. 5A-5D.

In some implementations, the server device 108 includes at least one server 138 and at least one data store 140. In the example of FIG. 1, the server device 108 is intended to represent various forms of servers including, but not limited to a web server, an application server, a proxy server, a network server, and/or a server pool. In general, server systems accept requests for application services and provide such services to any number of client devices (e.g., the external device 104) over the network 106 to support monitoring of usage of the injection device 102. In some implementations, a user (such as a patient or a healthcare provider) can access the application services to analyze past and present data associated with the usage of the injection device 102. The past and present data associated with the usage of the injection device 102 can include dates of medicament injection, expelled doses per date and remaining amount of medicament within the injection device 102.

FIGS. 2A-2G depict example acoustic mechanisms 200 that can be used to execute implementations of the present disclosure. The example acoustic mechanisms 200 are used for generating acoustic signals including injection device data. The example acoustic mechanisms 200 generate an acoustic signal through the mechanical interaction of a moving element 202a, 202b, 202c, 202d, 202e, 202f, 202g with an inhibition element 204a, 204b, 204c, 204d, 204e, 204f, 204g.

The moving element 202a, 202b, 202c, 202d, 202e, 202f, 202g can be a portion of or an element attached to a plunger rod of an injection device, such as plunger rod 118 described with reference to FIGS. 1A-1H. The moving element 202a, 202b, 202c, 202d, 202e, 202f, 202g can be configured to perform an axial (longitudinal or transversal) displacement (FIGS. 2A-2D), a rotation (FIGS. 2E-2G) or a combination of both. The moving element 202a, 202b, 202c, 202d can include an obstacle 206a, 206b, 206c, 206d, 206e, 206f, 206g. As illustrated in FIGS. 2A-2D, the obstacle 206a, 206b, 206c, 206d defines to a portion of the moving element 202a, 202b, 202c, 202d that includes a variation (increase or decrease) of the cross-sectional width of the moving element 202a, 202b, 202c, 202d relative to the beam width. The obstacle 206a, 206b, 206c, 206d can have a symmetric or asymmetric (sectioned) conical shape or (sectioned) pyramidal shape with smooth or sharp edges. As illustrated in FIGS. 2E-2G, the obstacle 206e, 206f, 206g defines to a portion of the moving element 202e, 202f, 202g that includes a variation (increase or decrease) of the radius of the moving element 202e, 202f, 202g.

The inhibition element 204a, 204b, 204c, 204d, 204e, 204f, 204g can be a portion of or an element attached to a housing of an injection device, such as housing 110 described with reference to FIGS. 1A-1H. In a non-actuated state, the edges of the inhibition element 204a, 204b, 204c, 204d, 204e, 204f, 204g can be at a distance from the edges of the moving element 202a, 202b, 202c, 202d, 202e, 202f, 202g. In an actuated state (during a movement of moving element 202a, 202b, 202c, 202d, 202e, 202f, 202g), a portion of the inhibition element 204a, 204b, 204c, 204d, 204e, 204f, 204g touches a portion of the moving element 202a, 202b, 202c, 202d, 202e, 202f, 202g. The inhibition element 204a, 204b, 204c, 204d, 204e, 204f, 204g can include a static portion (e.g., base of the inhibition element 204a, 204b, 204c, 204d, 204e, 204f, 204g) that is attached to a static component of an injection device (e.g., housing). The inhibition element 204a, 204b, 204c, 204d, 204e, 204f, 204g can include a movable portion (e.g., end of the inhibition element 204a, 204b, 204c, 204d, 204e, 204f, 204g) that is configured to move in response to a mechanical collision with the corresponding moving element 202a, 202b, 202c, 202d, 202e, 202f, 202g. The inhibition element 204a, 204b, 204c, 204d, 204e, 204f, 204g can include a single sided lever snapper (FIGS. 2A. 2E, and 2F), a dual-sided lever (FIG. 2B), a spring powered element (FIG. 2C), a recessed lever (FIGS. 2D and 2G).

FIGS. 3A-3I depict example acoustic mechanisms 300 that can be used to execute implementations of the present disclosure. The example acoustic mechanisms 300 are used for generating acoustic signals with unique acoustic signatures associated with particular injection device data. The example acoustic mechanisms 300 generate an acoustic signal through the mechanical interaction of a moving element 302a, 302b, 302c, 302d, 302e, 302f, 302g, 302h, 302i with an inhibition element 304a, 304b, 304c, 304d, 304e, 304f, 304g, 304h, 304i. The acoustic signatures are generated by modifying one or more acoustic features of the moving element 302a, 302b, 302c, 302d, 302e, 302f, 302g, 302h, 302i or the inhibition element 304a, 304b, 304c, 304d, 304e, 304f, 304g, 304h, 304i.

The acoustic features can include geometrical features (e.g., FIGS. 3A, 3E, 3G, 3H, and 3I), composition materials (e.g., FIGS. 3C and 3F), swinging elements (e.g., FIG. 3D), damping elements, flexible elements, single mode or multi-mode vibrating elements, number of moving elements 302a, 302b, 302c, 302d, 302e, 302f, 302g, 302h, 302i and/or number of inhibition element 304a, 304b, 304c, 304d, 304e, 304f, 304g, 304h, 304i. The geometrical features can include double- or multi-click features (e.g., FIG. 3A), edge shapes (e.g., FIGS. 3E, 3G, and 3H), changes of dimensions (e.g., length, width, beam width, curvature, etc.), single split features, multiple split features (e.g., FIG. 3I) or a combination of features.

The composition materials used to generate an acoustic signature can include different types of plastics, metals or a combination of both. For example, one or both of the moving element 302a, 302b, 302c, 302d, 302e, 302f, 302g, 302h, 302i and the corresponding inhibition element 304a, 304b, 304c, 304d, 304e, 304f, 304g, 304h, 304i can be made of selected composition materials (e.g., FIG. 3C, 3E). As another example, one or both of the moving element 302a, 302b, 302c, 302d, 302e, 302f, 302g, 302h, 302i and the corresponding inhibition element 304a, 304b, 304c, 304d, 304e, 304f, 304g, 304h, 304i can be made of a first composition material and can include a deposition of a second material different from the first material (e.g., printed ink or deposited metal) onto the first composition material (e.g., FIG. 3F).

As illustrated in FIG. 3B, the inhibition element 304b can have a pre-tension of a particular intensity, which generates an acoustic signal with a particular acoustic signature in response to collision with the obstacle of the moving element 302b. As illustrated in FIG. 3D, the use of a swinging element 306d can dampen (e.g., attenuate) the acoustic signal or generate reverberations. In some implementations, particular types of composition materials are selected such that acoustic attenuation can be frequency-dependent.

FIGS. 4A-4C depict example acoustic mechanisms 400 that can be used to execute implementations of the present disclosure. The example acoustic mechanisms 400 are used for time or frequency-domain encoding of acoustic signals associated with a particular injection device data. The example acoustic mechanisms 400 generate an acoustic signal through the mechanical interaction of a moving element 402a, 402b, 402c with an inhibition element 404a, 404b, 404c. The time-domain encoding or the frequency-domain encoding can be generated by modifying one or more acoustic features of the moving element 402a, 402b, 402c or the inhibition element 404a, 404b, 404c.

As illustrated in FIG. 4A, the moving element 402a can be a rotating wheel with multiple obstacles or indents of (two) different heights. The heights can be selected such that during the rotation of the wheel, the lever 404a can generate a click (e.g., an acoustic signal with a single maximum) at the interaction with the tall obstacles and not touch the short obstacles. The distance between obstacles can be constant and the width of the obstacles can be constant, such that the height of the obstacles can be used as a binary value. The acoustic signal 406a includes a sequence of binary values that encodes in the time domain the drug type and/or an identifier of the injection device.

As illustrated in FIG. 4B, the lever 404b can have a sequential deposition of different materials within regions of different widths and thicknesses that are equidistant from each other. The type of composition material used for a deposition segment corresponds to a binary value in the frequency domain. The interaction between the lever 404b and an obstacle 402b, during the movement of either the lever 404b and/or the obstacle 402b, generates an acoustic signal 406b encoded in the frequency domain.

As illustrated in FIG. 4C, the obstacle 402c can include a plurality of vibrating elements that are equidistant from each other. The length of a vibrating element dictates the resonance frequency corresponding to that vibrating element. The interaction between the lever 404c and an obstacle 402c, during the movement of either the lever 404c and/or the obstacle 402c, generates an acoustic signal 406c encoded in the frequency domain.

FIGS. 5A-5D illustrate block diagrams of example systems 500 that can execute implementations of the present disclosure. The system 500 enables transmission of signals between an injection device 102 and an external device 104. In the example illustrated in FIG. 5A, the injection device 102 includes an acoustic source 502. The acoustic source 502 is configured to generate acoustic signals encoding injection device data, as described with reference to FIGS. 1-4. The acoustic signals are generated by the acoustic source 502 within a range detectable by the external device 104. The external device 104 includes an in/out module 504 and a control module 506.

The in/out module 504 can be a standard component of the external device 104 that is controlled by the control module 506 to support communication with the injection device and the processing of the acoustic signals. The in/out module 504 includes a microphone 508, an audio to digital (AD) converter 510, a display 512, a hardware driver 514, and a memory 516. The display 512 can be configured to enable a user of the external device 104 to interact with the external device 104 by providing user input and receiving indications associated with the injection device 102 and the treatment performed using the injection device 102. The hardware driver 514 includes a program that controls the display 512. The memory 516 can be a computer-readable medium configured to store data, including acoustic signals received by the microphone 508 and results of processing the acoustic signals generated by the control module 506.

The control module 506 can be an application downloadable from a server that is configured to control one or more operations of the external device 104. For example, the operation of the external device 104 is controlled by programs executed by the control module 506. The control module 506 includes an activation component 518, a detection component 520, and an analysis component 522. The activation component 518 can be configured to generate an activation signal that can start a communication process with the injection device 102, as described with reference to FIGS. 1A-1H. The activation of the communication process is an important factor contributing to the energy consumption of the external device 104, the usability and the reliability of the detection in the proximity of the external device 104.

In some implementations, the activation signal is generated in response to receiving a wake signal. The wake signal can include a word spoken by a user of the external device 104 or a specific acoustic noise generated by an operation of the injection device 102 (e.g., a noise associated with a priming operation, a dose dialing click or a dispense click). In some implementations, the activation signal is generated in response to receiving a user input from the in/out module 504 that includes a request to initiate the communication process with the injection device 102. In some implementations, the activation signal is generated at a preset frequency (e.g., once or multiple times a day) that can be updated by a user of the external device 104 to correspond with a treatment schedule. In some implementations, prior to activating the communication process, the activation component 518 provides a user of the external device 104, though the in/out module 504, with a message requesting approval to initiate the communication process with the injection device 102.

The detection component 520 can be configured to generate a detection signal to control the detection of acoustic signals using the microphone 508. In some implementations, the detection process can be controlled based on one or more parameters of the activation process. For example, the detection component 520 can be configured to communicate with the activation component 518 to initiate detection operations at a particular time after the activation component 518 generated the trigger signal. The detection operations can include a pre-processing phase (e.g., normalization of the signal amplitude, stretching of the signal on the time scale, echo cancellation and/or reverberation suppression, removal of background noise, identifications of regions of interest), an actual detection phase, and a post-processing phase (e.g., data range validation and/or plausibility checks). In some implementations, the detection component 520 activates a filter (e.g., a bandpass filter and/or a band-reject filter) included in the external device 104 during the detection of the modulated RF signal.

The analysis component 522 can be configured to generate an analysis signal to control the analysis of the acoustic signals detected by the microphone 508. For example, the analysis component 522 can control the selection of a signal processing algorithm used to process the acoustic signals and to generate an output data. The signal processing algorithm can include one or a combination of basic signal processing methods (e.g., discrete Fourier transform, short-time Fourier transform, discrete cosine transform, discrete-time wavelet transform), short- and mid-term feature extraction, classifiers (e.g., k-nearest-neighbor classifier, decision tree, support vector machine, artificial neural network, deep neural network), algorithms based on a-priori knowledge of the expected signal to 'train' the algorithm and algorithms based on a-priori knowledge of the expected signal to correlate received signals with expected signals to determine regions of interest. The output data can include a number of clicks, a drug type along with the timestamp available in the external device 104. The analysis component 522 can control one or more operations performed on the output data by sending it for storage to the memory 516, for display to the display component 512, or to an antenna for upload to a server.

Figure 5A:
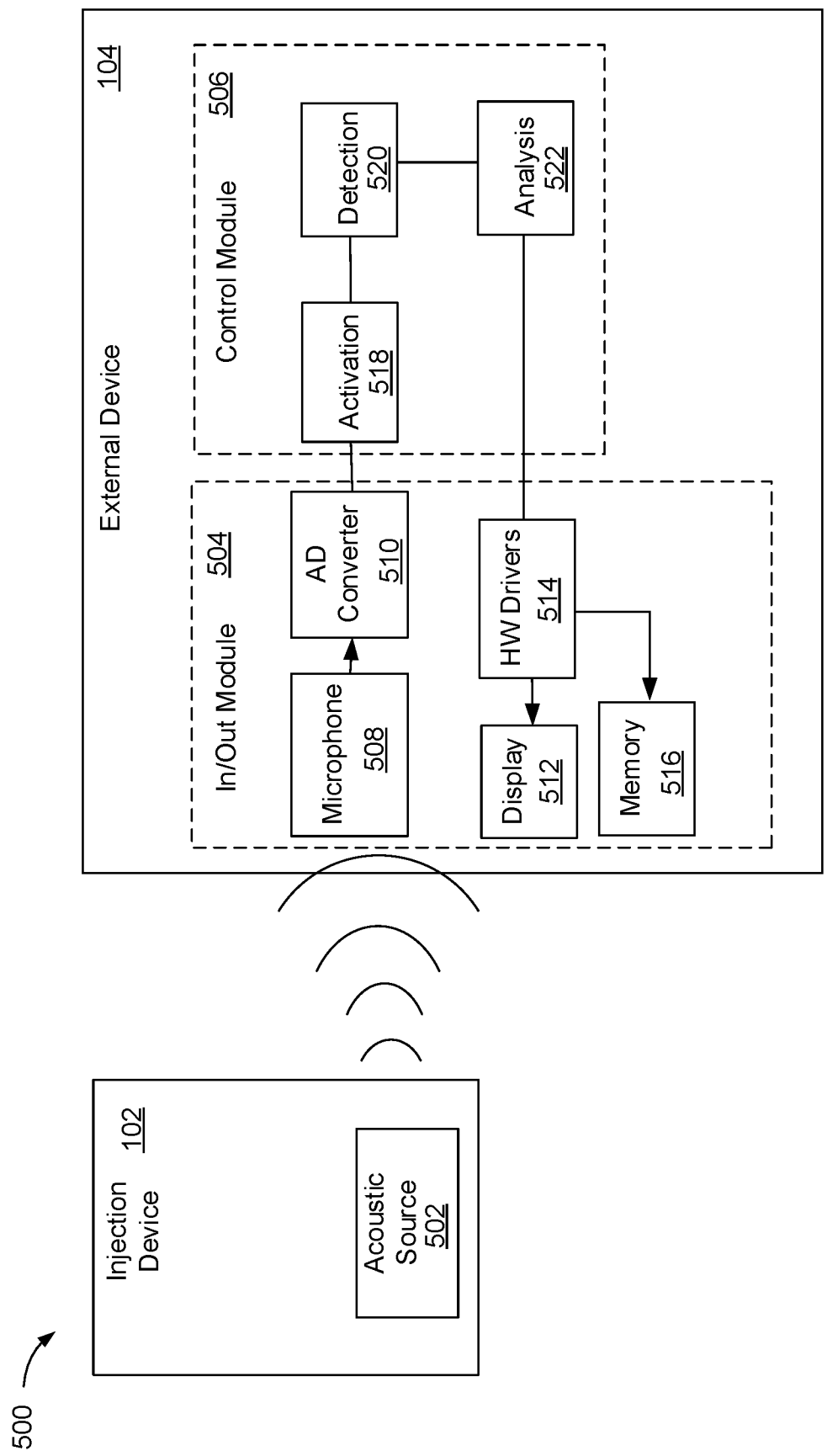
FIGS. 5A-5D are block diagrams of example system components that can execute implementations of the present disclosure.
Figure 5B:
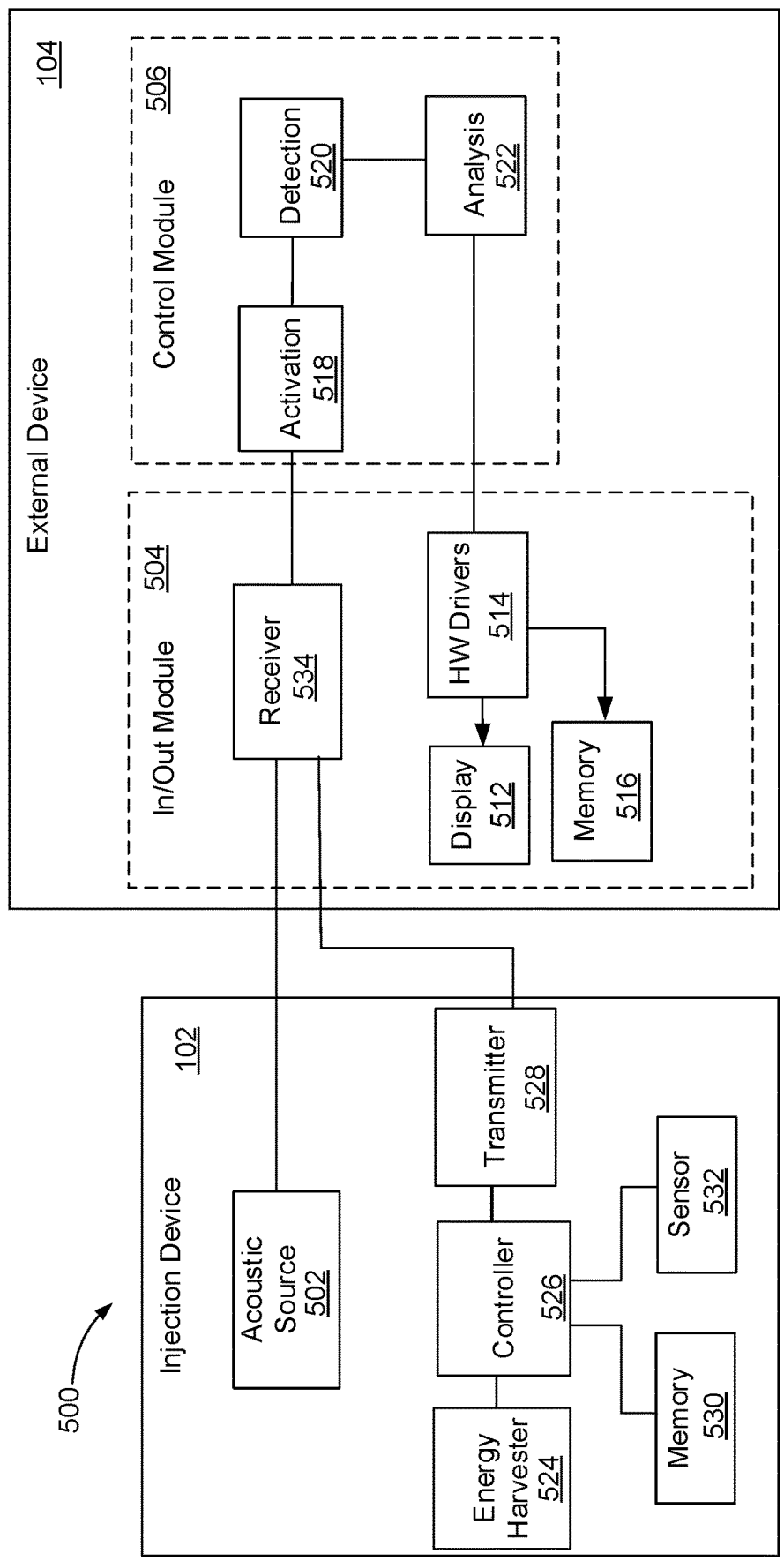

In the example illustrated in FIG. 5B, the injection device 102 is an electromechanical device. The example injection device 102 of FIG. 5B is configured for ultra-low-power radio frequency (RF) communication, based on ultra-wide band impulse radio (UWB IR) communication between the injection device 102 and the external device 104. The example injection device 102 of FIG. 5B, includes a plurality of electronic components and optionally includes the acoustic source 502. The electronic components include an energy harvester 524, a controller 526, a transmitter 528, a memory 530, and a sensor 532. The harvester 524 can be configured for harvesting energy from the RF signals generated by the external device 104. The harvester 524 can include an antenna configured to capture the RF signals, a piezoelectric crystal that generates an electrical pulse in response to receiving RF signals and a boost converter configured to increase the voltage level for use by the controller 526. The controller 526 can be a control component defining a junction point of the electronic components of the injection device 102. The controller 526 can process one or more signals received from the other electronic components of injection device 102. The controller 526 can trigger a measurement of the sensor 532 (e.g., a temperature sensor, a humidity sensor, and a fill level sensor). The controller 526 can transmit a signal to the transmitter 528 to trigger a transmission of data to the external device 104.

The memory 530 can include a microcontroller, a microprocessor or a combination of microprocessor components and other components formed in a single package. The memory 530 can be an arithmetic and/or a logic unit array. For example, the memory 530 can be configured to execute operations on sensor data to generate output data. The memory 530 can be configured for low power consumption such that it can operate using the energy supplied by the energy harvester 524. For example, the memory 530 can include one or more of an electrically erasable programmable read-only memory (EEPROM), static random access memory (SRAM), ferroelectric random access memory (FRAM), magnetoresistive random access memory (MRAM), and phase change memory (PCM). FRAM is a non-volatile random-access memory, which is based on the integration of a ferroelectric material to achieve non-volatility. FRAM does not require a special sequence to write data nor does it require a charge pump to achieve the higher programming voltages (e.g., FRAM programs at I 0.5V). FRAM has the advantage of low power consumption (e.g., lower than EEPROM), low write voltage requirements, fast write speeds and a large number of write-erase cycles. FRAM is compatible to standard CMOS processes, which means that it can be integrated with other logic functions into the injection device 102, by implementing additional processing steps. MRAM provides fast read/write speeds in the order of approximately 35 ns, long data retention and an unlimited number of read/write cycles. Reads of MRAM are not destructive.

The transmitter 528 can be configured to automatically transmit data using UWB IR signals to the external device 104. In some implementations, the transmission is performed automatically, in response to receiving an injection device data from the controller 526. The in/out module 504 of the external device 104 includes a receiver 534 configured to detect signals transmitted by the injection device 102. The receiver 534 can include a microphone configured to detect acoustic signals generated by the acoustic source 502 and an ultra-wide band receiver configured to detect UWB IR signals generated by the transmitter 528. The receiver 534 transmits the detected signals to the control module 506, which processes the signals as described with reference to FIG. 5A.

Figure 5C:
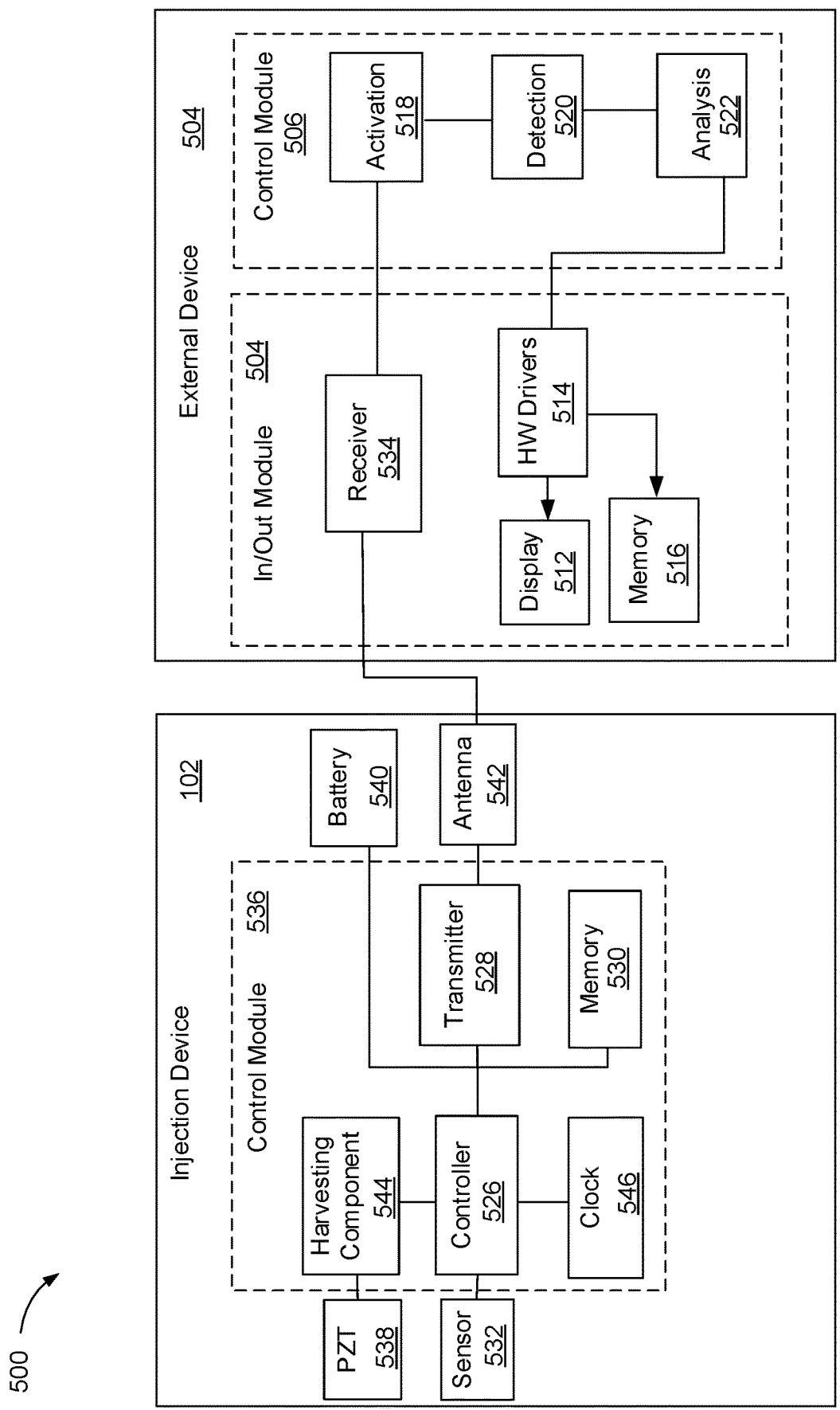

In the example illustrated in FIG. 5C, the injection device 102 is an electromechanical device. The example injection device 102 of FIG. 5C is configured for ultra-low-power RF communication, based on ultra-wide band impulse radio communication between the injection device 102 and the external device 104. The example injection device 102 of FIG. 5C, includes a control module 536, a piezoelectric element 538, a sensor 532, a battery, 540 and an antenna 542. The control module 536 includes a harvesting component 544, a controller 526, a clock 546, a transmitter 528 and a memory 530.

The harvesting component 544 is configured to collect energy from one or more external sources and convert the collected energy to electrical energy. This energy may be stored or used directly to power other electronic components of the injection device 102. The harvesting component 544 includes an interface to an energy source, an energy converter, a DC/DC converter, and a load or a storage. Examples of interfaces include: an antenna designed for a specific frequency together with a matching network, a mechanical connection to a moveable magnet or a piezo crystal, a mechanical connection to a piezo crystal, and a thermocoupling to the heat source. The energy converter is configured to generate usable electrical energy from the energy source. Examples of energy converters include: a moving magnet that induces a current in a coil, a piezo crystal that generates an electrical pulse, and a charge pump that accumulates electrical charge.

The energy source can be associated with a user interaction with a component of the injection device 102. For example, the energy source can be a mechanical energy generated by a user rotating a dialing knob, pressing a button, and removal or replacement of a cap. The motion generated by the user can be mechanically coupled to the energy converter. The energy converter can be configured to use the torque delivered by the user to generate electrical energy. In some implementations, the energy converter can be attached to a spring that can store the mechanical energy generated by the interaction of the user and provide the stored energy upon request to the energy converter. The DC/DC converter is configured to adjust the generated voltage to a voltage level suitable for the load, for example from 0.5V to 5V. The load or storage can include a capacitor that provides a short-term storage for the harvested energy. In some implementations, the load may be directly attached to the DC/DC converter.

The sensor 532 can include one or more of multiple sensor types, such as a dialed dose sensor configured to generate an absolute value, a dose change sensor configured to generate an incremental value, a dispensed dose sensor configured to generate an incremental value, and a dispense button sensor configured to generate a binary value (button pressed or not pressed). The dialed dose sensor can be configured to trace a rotation resistance. The dose change sensor can include a piezoelectric element, a piezoelectric speaker, or a Wiegand sensor. The dose change sensor can be the piezoelectric element 538. The dose change sensor can be configured to count the number of clicks within an acoustic signal generated by a user interacting with an acoustic element of the injection device 102. The dispensed dose sensor can be configured to detect the dose based on an electrical contact.

The transmitter 528 is configured for generating UWB IR signals that enable communications between the injection device 102 and the external device 104. The UWB IR include very short RF pulses (e.g., smaller than 1 ns) covering a large portion of the radio spectrum (e.g., bandwidth larger than 500 MHz or 20% of the center frequency, whichever is lower), at a very low energy level. The operating frequency is chosen in accordance with one or more national and federal regulations. For example, a frequency band with wide international acceptance is from about 6.5 GHz to about 8 GHz. In some implementations, the UWB IR signals include a UWB IR standard widely accepted and available in smartphones from large vendors such that standard smartphone can be used as the external device 104.

In some implementations, the UWB IR communication includes a proprietary UWB protocol. The proprietary UWB protocol uses an encoding, which consists of a combination of time modulation, signal shape modulation, and amplitude modulation. A proprietary UWB device (e.g. USB dongle for a smartphone) can be used as the external device 104. The transmitter 528 generation of UWB IR is triggered by a user operation of the injection device 102 controlled by the controller 526 based on time signals received from the clock 546. The clock can include one or more of mechanical resonant devices (e.g., crystals and ceramic resonators) and electrical phase-shift circuits (e.g., resistor-capacitor oscillators and silicon oscillators).

The antenna 542 is configured for transmission of UWB IR signals. The antenna 542 is configured such that the time characteristics UWB IR are constant over the frequency spectrum, resulting in minimal pulse distortion. The antenna 542 exhibits a flat frequency spectrum, resulting in wide pulses with minimal resonant distortion. The antenna 542 is integrated into the injection device 102 near the surface of the housing 110 to have minimal attenuation of the signal. The antenna 542 is electrically insulated from the surface of the housing 110 to prevent user interaction from influencing the signal and signal strength. Possible implementations of the antenna 542 are the integration of a chip antenna, or the integration of a conductive layer acting as the antenna on one of the plastic parts of the injection device 102. The external device 104 can constantly or intermittently listen for incoming data packets transmitted by the antenna 542. Depending on the detection and storage concept, the transmission is performed once per injection, once per dose change or several times.

Figure 5D:
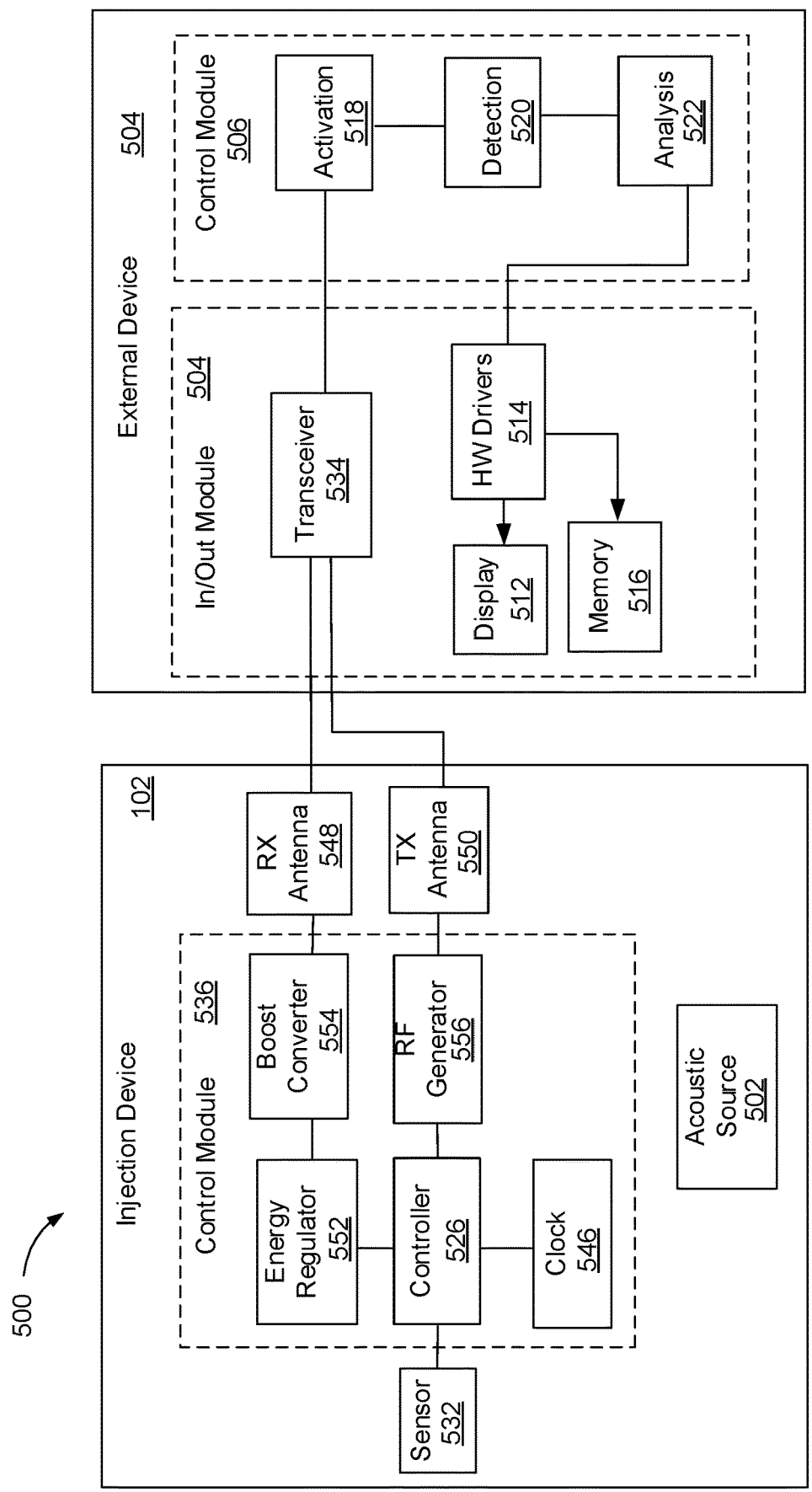

In the example illustrated in FIG. 5D, the injection device 102 is an electromechanical device. The example injection device 102 of FIG. 5B is configured for millimeter wave radio frequency (mm Wave RF) communication with the external device 104. The example injection device 102 of FIG. 5B, is a battery less device that includes a sensor 532, a control module 536, a receiving (RX) antenna 548, a transmitting (TX) antenna 550, and, optionally, the acoustic source 502. The control module 536 includes a boost converter 554, an energy regulator 552, a controller 526, a clock 546, and a RF generator 556.

The RX antenna 548 can be configured for harvesting energy from the RF (mm wave) signals generated by the transceiver 534 of the external device 104 within a communication range larger than about 50 cm to about 1 m. The operating frequency is chosen in accordance with one or more national and federal regulations. For example, a frequency band with wide international acceptance is about 60 GHz. In some implementations, the RF (mm wave) signals include a RF (mm wave) standard widely accepted and available in smartphones from large vendors such that standard smartphone can be used as the external device 104. In some implementations, the RF (mm wave) communication includes a proprietary RF (mm wave) protocol. The proprietary RF (mm wave) protocol uses an encoding, which consists of a combination of time modulation, signal shape modulation, and amplitude modulation. A proprietary RF (mm wave) device (e.g. USB dongle for a smartphone) can be used as the external device 104. The RX antenna 548 can include a very small (e.g., a few millimeters wide) antenna configured to capture the RF (mm wave) signals. The RX antenna 548 can be integrated into the injection device 102 near the surface of the housing 110 to have minimal attenuation of the signal. The RX antenna 548 can be electrically insulated from the surface of the housing 110 to prevent user interaction from influencing the signal and signal strength. Possible implementations of the RX antenna 548 are the integration of a chip antenna, or the integration of a conductive layer acting as the antenna on one of the plastic parts of the injection device 102. The energy captured by the RX antenna 548 is transmitted to the boost converted 554. The boost converted 554 is configured to boost the generated voltage to a voltage level suitable for the energy regulator 552, which further provides regulated energy to the controller 526.

The controller 526 can trigger a measurement of the sensor 532 (e.g., a temperature sensor, a humidity sensor, and a fill level sensor). The controller 526 can transmit a sensor measurement to the RF generator 556 to generate an RF (mm wave) signal based on the sensor measurement. In some implementations, the generation of RF (mm wave) signals is performed automatically, in response to receiving the sensor measurement from the controller 526. The RF (mm wave) signals are transmitted by the TX antenna 550 to the transceiver 534. The transceiver 534 can include a microphone configured to detect acoustic signals generated by the acoustic source 502 and RF (mm wave) receiver configured to detect RF (mm wave) signals transmitted by the TX antenna 550. The transceiver 534 transmits the detected signals to the control module 506, which processes the signals as described with reference to FIGS. 5A-5C.

Figure 6:
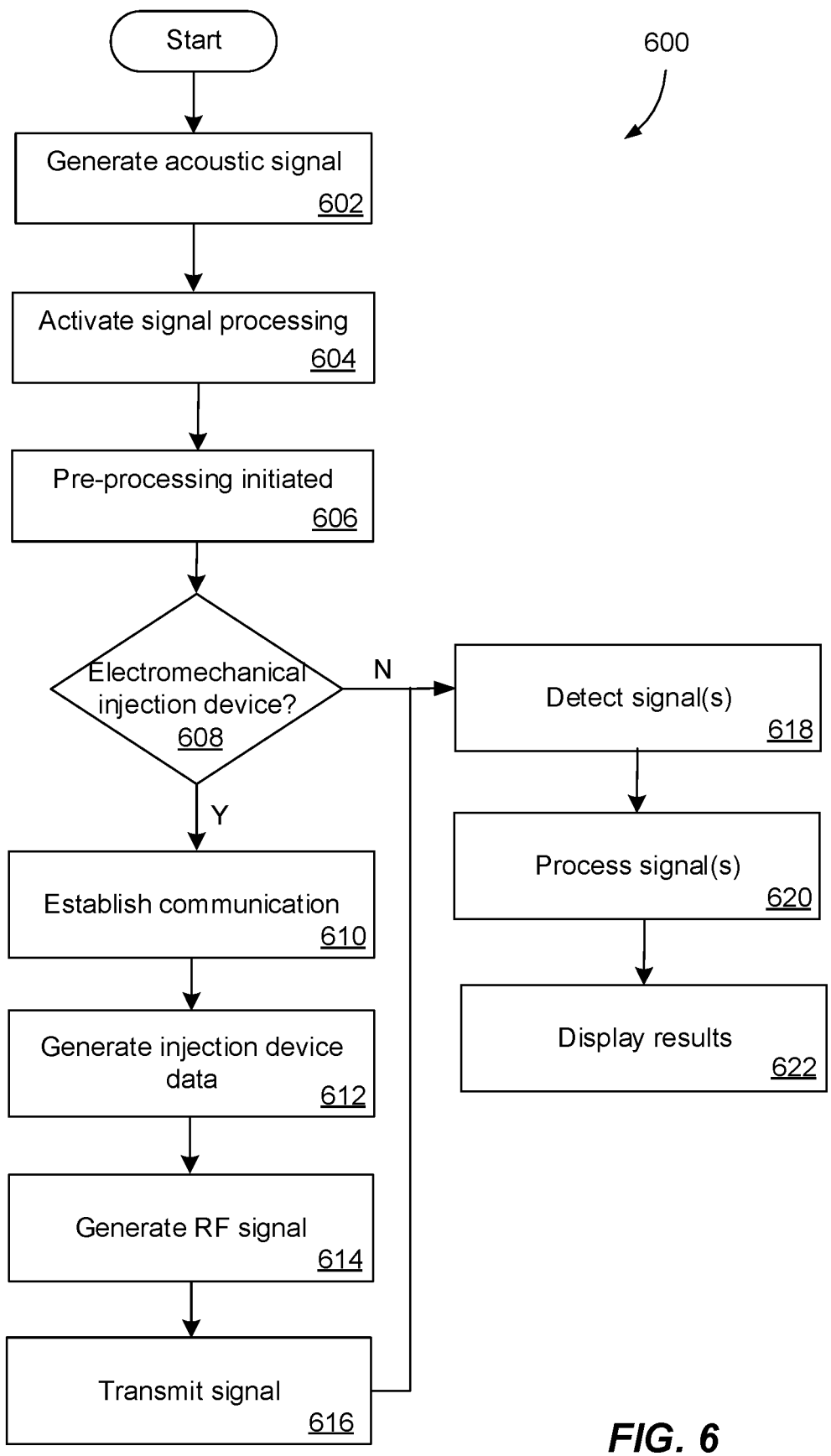
FIG. 6 is a flowchart illustrating an example process that can be executed to perform operations of the present disclosure.

FIG. 6 is a flowchart illustrating an example process 600 that can be executed by devices and systems described with reference to FIGS. 1-5. The process 600 begins by generating an acoustic signal using an acoustic source of an injection device (602). The acoustic signal can be generating during an operation including a user actuating the acoustic source of the injection device. The acoustic sources can include pressure elements (e.g., buttons), rotating elements (e.g., rotating knobs, rotating cams, or rotating wheels), inhibition elements (e.g., protrusions), vibration elements, latching elements, flexible elements, swinging elements, attenuation elements, and other mechanical elements, as described in detail with reference to FIGS. 2-4. The operation can be a priming operation, a dose dispense operation, a cap removal operation, a recapping operation, an on-off switch actuation or any other type of operation including a transfer of a mechanical energy though an acoustic source. The acoustic signal can include multiple acoustic signals generated by multiple acoustic sources. For example, the acoustic signals can include data associated with an amount of medicament dispensed by the injection device, an amount of medicament remaining in the medicament reservoir of the injection device, and/or an identifier of the injection device. The acoustic signals can be encoded in time-domain or in the frequency-domain.

In response to generating the acoustic signal, a signal processing application is launched by the external device (604). The signal processing application can include a plurality of operations to be performed by multiple components of the external device. The first operation of the signal processing application includes a pre-processing operation (606). The pre-processing operation can include activation of one or more filters to perform normalization of the signal amplitude, stretching of the signal on the time scale, echo cancellation and/or reverberation suppression, removal of background noise, and/or identifications of regions of interest within the signal.

Further, it is determined, by the external device, whether the injection device is a mechanical device including only mechanical components or an electromechanical device including both mechanical components and electronic components (608). In some implementations, the identifier of the injection device (included in the acoustic signal) indicates the type of injection device. In some implementations, a user input on the external device indicates the type of the injection device.

If the injection device is an electromechanical device, the acoustic signal can be used as a trigger to initiate a communication between the injection device and the external device (610). During established communication between the injection device and the external device, the injection device can be configured to harvest energy from interrogation signals transmitted by the external device. Harvesting energy can include generating, by a RF harvester, an electric signal based on an ultra-wide band or millimeter wave RF signal received by an antenna of the injection device. In some implementations, the harvested energy is boosted for voltage increase. The electrical energy is used to power a control component configured control operation of other electronic components. For example, the controller can determine whether the received electric energy is sufficient to activate one or more additional components of the injection device. If it is determined that additional energy is necessary, supplemental energy can be retrieved from one or more of a rechargeable battery, a capacitor and an energy harvester. Retrieving the supplemental energy can include harvesting energy from additional sources different from the RF signal. The supplemental energy can be combined with the RF generated energy and directed towards the controller. In response to determining that the energy is sufficient, one or more additional components of the injection device are activated to initiate sensor measurement. Sensor measurements can include detection of an indication associated with a function of the injection device to generate a sensor signal. The indication can include a mechanical signal, an acoustic signal, an optical signal, a magnetic signal, an electric signal, or a combination thereof generated before, during or after the function of the device. The function of the injection device can include a movement of the plunger rod, a displacement of the plunger head, a dose selection or other operations associated with dispensing of the medicament. The indication can be converted by a sensor into a sensor signal. The controller can be configured to receive the sensor signal generated by the sensor. The controller can process the sensor signal to generate injection device data (612). The injection device data can include acoustic signals, sensor signals from a plurality of sensors and additionally stored data. For example, the injection device data can include a unique identifier for the injection device, an amount of administered medicament, an amount of medicament within a medicament reservoir, a medicament temperature, a timestamp of administering the medicament, a location, and/or a situation specific data for the injection device.

The injection device data can be transmitted, by the controller, to an RF generator to convert the data to an ultra-wide band or millimeter wave RF signal (614). It is determined whether the injection device has sufficient energy to power the antenna to transmit the RF signal associated with the injection device data to the external device. If it is determined that additional energy is necessary, supplemental energy can be retrieved from one or more of the rechargeable battery, the capacitor and the energy harvester. If it is determined that the antenna has sufficient energy, the antenna is powered and the ultra-wide band or millimeter wave RF signal is transmitted to the external device (616).

In response to signal transmission, the signals generated by the injection device are detected by the external device (618). For example, if the injection device is a mechanical device, the external device detects only acoustic signals. If the injection device is an electromechanical device, the external device detects ultra-wide band or millimeter wave RF signal and, optionally, additional acoustic signals transmitted by the injection device. The detection operations can include recording of the detected signals transmitted by the injection device. In some implementations, detection operations can include applying a filter (e.g., a bandpass filter and/or a band-reject filter) to the detected signal before recording the detected signal.

In response to signal detection, the signals are post-processed to generate injection device results (620). Post-processing can include operations that integrate previously stored injection device data (e.g., determining an amount of expelled medicament based on medicament volume comparisons, determining a variation of treatment protocol), range validation, and/or plausibility checks. The injection device results are displayed by a display of the external device (622). In some implementations, if the injection device is an electromechanical device, in response to displaying the results, the communication between the injection device and the external device is terminated.

Figure 7:
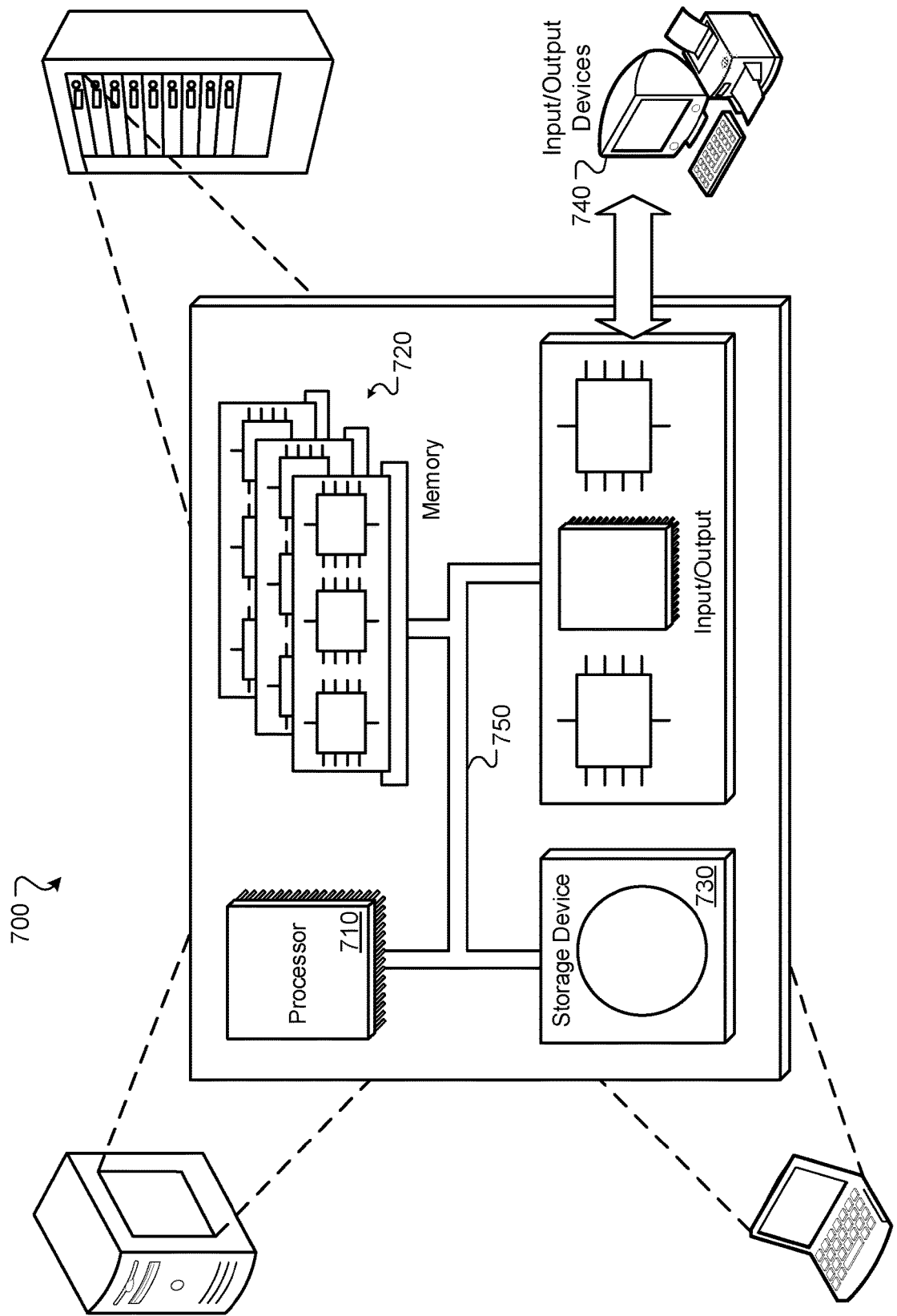
FIG. 7 is a schematic illustration of example computer systems that can be used to execute implementations of the present disclosure.

FIG. 7 shows a schematic diagram of an example computing system 700. The system 700 can be used for the operations described in association with the implementations described herein. For example, the system 700 may be included in any or all of the server components discussed herein. The system 700 includes a processor 710, a memory 720, a storage device 730, and an input/output device 770. Each of the components 710, 720, 730, and 770 are interconnected using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 770.

The memory 720 stores information within the system 700. In one implementation, the memory 720 is a computer-readable medium. In one implementation, the memory 720 is a volatile memory unit. In another implementation, the memory 720 is a non-volatile memory unit. The storage device 730 is capable of providing mass storage for the system 700. In one implementation, the storage device 730 is a computer-readable medium. In various different implementations, the storage device 730 may be a floppy disk device, a hard disk device, an optical disk device, or a tape device. The input/output device 770 provides input/output operations for the system 700. In one implementation, the input/output device 770 includes a keyboard and/or pointing device. In another implementation, the input/output device 770 includes a display unit for displaying graphical user interfaces that enable a user to access data related to an item that is collected, stored and queried as described with reference to FIGS. 1-6.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a OLED (organic light-emitting diode) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

A number of implementations of the present disclosure have been described. Nevertheless, it will be understood that various modifications may be made without departing from the spirit and scope of the present disclosure. Accordingly, other implementations are within the scope of the following claims.

The invention claimed is:

1. A medicament injection system comprising:
an injection device comprising:
a medicament reservoir configured to store a medicament to be expelled by the injection device;
an acoustic source configured to generate an acoustic signal comprising information indicative of an amount of the medicament stored in the medicament reservoir, wherein a portion of a wall of the injection device that is proximal to the acoustic source defines an opening configured to enhance transmission of the acoustic signal; and
an external device comprising:
an acoustic receiver configured to record the acoustic signal; and
one or more processors configured to process the recorded acoustic signal and to generate injection device data based on the processed recorded acoustic signal,
wherein the external device is configured to display information based on the injection device data.

2. The medicament injection system of claim 1, wherein the acoustic source comprises a moving element and an inhibition element that produce the acoustic signal by interacting with each other.

3. The medicament injection system of claim 2, wherein the moving element comprises at least one of a lever-type snapper, a dual-sided lever, a spring-powered element, a rotating cam, and a rotating wheel comprising multiple indents.

4. The medicament injection system of claim 2, wherein at least one of the moving element and the inhibition element comprises an arrangement of a plurality of materials to generate a sequence of a plurality of frequencies.

5. The medicament injection system of claim 2, wherein at least one of the moving element and the inhibition element comprises a plurality of geometrical features to generate a sequence of a plurality of frequencies.

6. The medicament injection system of claim 5, wherein the sequence of the plurality of frequencies is associated with an identifier of the injection device.

7. The medicament injection system of claim 1, wherein the acoustic source is enclosed within the injection device.

8. The medicament injection system of claim 1, wherein the opening is covered by a sealing membrane.

9. The medicament injection system of claim 1, wherein the acoustic source is attached to an exterior surface of the injection device.

10. The medicament injection system of claim 1, wherein the acoustic source is integrated into a dial grip to generate an omnidirectional transmission of the acoustic signal.

11. The medicament injection system of claim 1, wherein the acoustic signal includes an identifier of the injection device, wherein the acoustic source includes a vibrating element configured to generate reverberation within the acoustic signal, and wherein the reverberation is associated with the identifier of the injection device.

12. The medicament injection system of claim 11, wherein the external device is configured to use the identifier to uniquely the injection device and to display information based on the injection device data.

13. An injection device comprising:
a medicament reservoir configured to store a medicament to be expelled by the injection device;
an acoustic source configured to generate an acoustic signal comprising information indicative of an amount of the medicament stored in the medicament reservoir, wherein a portion of a wall of the injection device that is proximal to the acoustic source defines an opening configured to enhance transmission of the acoustic signal;
an acoustic receiver configured to record the acoustic signal;
a control logic configured to process the recorded acoustic signal and to generate injection device data based on the processed recorded acoustic signal; and
an antenna configured to transmit the injection device data to an external device that is configured to display information based on the injection device data.

14. The injection device of claim 13, wherein the acoustic signal includes an identifier of the injection device, wherein the acoustic source includes a vibrating element configured to generate reverberation within the acoustic signal, and wherein the reverberation is associated with the identifier of the injection device.

15. The injection device of claim 14, wherein the antenna is configured to transmit the injection device data to an external device that is configured to use the identifier to identify the injection device and to display information based on the injection device data.

16. A medicament injection system comprising:
an injection device comprising:
a medicament reservoir configured to store a medicament to be expelled by the injection device;
an acoustic source configured to generate an acoustic signal comprising information indicative of an amount of the medicament stored in the medicament reservoir, wherein a portion of a wall of the injection device that is proximal to the acoustic source defines an opening configured to enhance transmission of the acoustic signal;

an acoustic receiver configured to record the acoustic signal;

a control logic configured to process the recorded acoustic signal and to generate an injection device signal based on the processed recorded acoustic signal; and an antenna configured to transmit the injection device signal; and an external device comprising:

a receiver configured to receive the injection device signal; and one or more processors configured to process the injection device signal and to generate injection device data based on the processed injection device signal, wherein the external device is configured to display information based on the injection device data.

17. The medicament injection system of claim 16, wherein the acoustic source comprises a moving element and an inhibition element that produce the acoustic signal by interacting with each other.

18. The medicament injection system of claim 17, wherein the moving element comprises at least one of a lever-type snapper, a dual-sided lever, a spring-powered element, a rotating cam, and a rotating wheel comprising multiple indents.

19. The medicament injection system of claim 17, wherein at least one of the moving element or the inhibition element comprises an arrangement of a plurality of materials to generate a sequence of a plurality of frequencies.

* * * * *